United States Patent
Dreilinger et al.

(10) Patent No.: US 11,812,966 B2
(45) Date of Patent: Nov. 14, 2023

(54) CLIPS, APPLIERS, AND CARTRIDGES

(71) Applicant: NeuraMedica Inc., Oregon City, OR (US)

(72) Inventors: Rachel Dreilinger, Beavercreek, OR (US); Neil Roundy, Eugene, OR (US); Mariah Knight, Cornelius, OR (US); Sandra Baker, Tigard, OR (US)

(73) Assignee: NeuraMedica Inc., Oregon City, OR (US)

(*) Notice: Subject to any disclaimer, the term of this patent is extended or adjusted under 35 U.S.C. 154(b) by 392 days.

(21) Appl. No.: 16/858,546

(22) Filed: Apr. 24, 2020

(65) Prior Publication Data
US 2021/0330328 A1    Oct. 28, 2021

(51) Int. Cl.
| | |
|---|---|
| *A61B 17/08* | (2006.01) |
| *A61B 17/122* | (2006.01) |
| *A61B 17/00* | (2006.01) |
| *A61B 17/04* | (2006.01) |

(52) U.S. Cl.
CPC ........ *A61B 17/083* (2013.01); *A61B 17/1222* (2013.01); *A61B 2017/00584* (2013.01); *A61B 2017/0488* (2013.01)

(58) Field of Classification Search
CPC ....... A61B 17/08; A61B 17/083; A61B 17/10; A61B 17/105; A61B 17/122; A61B 17/1222; A61B 17/1227; A61B 17/128; A61B 17/1285; A61B 2017/00584; A61B 2017/0488
See application file for complete search history.

(56) References Cited

U.S. PATENT DOCUMENTS

| | | | | |
|---|---|---|---|---|
| 640,517 | A * | 1/1900 | Acheson | A61B 17/1285 606/120 |
| 1,482,290 | A * | 1/1924 | Elzi | A01K 11/002 72/409.02 |
| 2,635,238 | A * | 4/1953 | Garland | A61B 17/122 29/268 |
| 2,652,832 | A | 9/1953 | Castroviejo | |
| 2,876,778 | A * | 3/1959 | Kees, Jr. | A61B 17/2812 606/208 |
| 3,032,039 | A * | 5/1962 | Beaty | A61B 17/122 227/19 |
| 3,254,649 | A * | 6/1966 | Wood | A61B 17/076 606/205 |
| 3,326,216 | A * | 6/1967 | Wood | A61B 17/128 606/208 |

(Continued)

FOREIGN PATENT DOCUMENTS

| | | |
|---|---|---|
| BR | 1120170091968 | 12/2021 |
| CA | 2133687 C | 3/2007 |

(Continued)

OTHER PUBLICATIONS

CN103989501A, Google Translation of CN103989501A, as early as Jun. 7, 2018, 7 pages.

(Continued)

*Primary Examiner* — Ryan J. Severson
(74) *Attorney, Agent, or Firm* — LAW OFFICE OF KAREN DANA OSTER, LLC

(57) ABSTRACT

A medical device forming method, an applier for manipulating clips, and a cartridge for holding clips are disclosed herein.

26 Claims, 25 Drawing Sheets

(56) References Cited

U.S. PATENT DOCUMENTS

| | | | |
|---|---|---|---|
| 3,378,010 A | 4/1968 | Codling | |
| 3,439,522 A * | 4/1969 | Wood | A61B 17/128 606/142 |
| 3,446,212 A * | 5/1969 | Le Roy | A61B 17/10 24/456 |
| 3,601,127 A | 8/1971 | Finegold | |
| 3,604,425 A | 9/1971 | Le Roy | |
| 3,805,792 A * | 4/1974 | Cogley | A61B 17/1227 606/142 |
| 4,076,120 A | 2/1978 | Carroll et al. | |
| 4,146,130 A | 3/1979 | Samuels et al. | |
| 4,187,712 A | 2/1980 | Samuels et al. | |
| 4,217,902 A | 8/1980 | March | |
| 4,294,355 A | 10/1981 | Jewusiak et al. | |
| 4,344,531 A | 8/1982 | Giersch | |
| 4,361,229 A | 11/1982 | Mericle | |
| 4,412,617 A | 11/1983 | Cerwin | |
| 4,447,943 A * | 5/1984 | Baucom | B29C 70/44 156/289 |
| 4,462,404 A * | 7/1984 | Schwarz | A61B 17/10 81/313 |
| 4,478,221 A | 10/1984 | Heiss | |
| 4,505,273 A | 3/1985 | Braun et al. | |
| 4,519,501 A | 5/1985 | Cerwin | |
| 4,696,396 A | 9/1987 | Samuels | |
| 4,744,365 A | 5/1988 | Kaplan et al. | |
| 4,793,349 A | 12/1988 | Weinrib | |
| 4,821,721 A | 4/1989 | Chin et al. | |
| 4,825,864 A | 5/1989 | Hariri | |
| 4,936,447 A | 6/1990 | Peiffer | |
| 4,938,214 A | 7/1990 | Specht et al. | |
| 4,961,499 A | 10/1990 | Kulp | |
| 4,971,198 A | 11/1990 | Mericle | |
| 4,972,949 A | 11/1990 | Peiffer | |
| 4,983,176 A | 1/1991 | Cushman et al. | |
| 5,007,921 A | 4/1991 | Brown | |
| 5,046,611 A | 9/1991 | Oh | |
| 5,047,049 A | 9/1991 | Salai | |
| 5,065,516 A | 11/1991 | Dulebohn | |
| 5,104,397 A | 4/1992 | Vasconcelos et al. | |
| 5,141,514 A * | 8/1992 | van Amelsfort | A01K 11/002 606/116 |
| 5,192,288 A | 3/1993 | Thompson et al. | |
| 5,201,416 A | 4/1993 | Taylor | |
| 5,207,692 A | 5/1993 | Kraus et al. | |
| 5,236,436 A | 8/1993 | Koros et al. | |
| 5,279,416 A | 1/1994 | Malec et al. | |
| 5,336,458 A | 11/1994 | Korthoff et al. | |
| 5,366,458 A | 11/1994 | Korthoff et al. | |
| 5,405,353 A | 4/1995 | Randall | |
| 5,425,489 A | 6/1995 | Shichman et al. | |
| 5,520,704 A | 5/1996 | Castro et al. | |
| 5,551,214 A | 9/1996 | Vincze et al. | |
| 5,591,178 A | 1/1997 | Green et al. | |
| 5,725,542 A | 3/1998 | Yoon | |
| 5,779,720 A | 7/1998 | Walder-Utz et al. | |
| 5,908,430 A | 6/1999 | Appleby | |
| 6,044,971 A | 4/2000 | Esposito et al. | |
| 6,120,526 A | 9/2000 | Daley | |
| 6,158,583 A | 12/2000 | Forster | |
| 6,273,253 B1 | 8/2001 | Forster et al. | |
| 6,283,984 B1 | 9/2001 | Ray | |
| D451,347 S | 12/2001 | Kleckauskas et al. | |
| 6,352,541 B1 | 3/2002 | Kienzle et al. | |
| 6,419,682 B1 | 7/2002 | Appleby et al. | |
| 6,425,903 B1 | 7/2002 | Voegele | |
| 6,460,700 B2 | 10/2002 | Weisshaupt | |
| 6,537,289 B1 | 3/2003 | Kayan et al. | |
| 6,679,894 B2 | 1/2004 | Damarati | |
| 6,880,699 B2 | 4/2005 | Gallagher | |
| 6,896,683 B1 * | 5/2005 | Gadberry | A61B 17/128 606/143 |
| 7,322,995 B2 * | 1/2008 | Buckman | A61B 17/122 606/157 |
| 7,533,790 B1 | 5/2009 | Knodel et al. | |
| 8,075,481 B2 | 12/2011 | Park et al. | |
| 8,312,992 B2 | 11/2012 | Disch | |
| 8,393,517 B2 | 3/2013 | Milo | |
| 8,398,655 B2 | 3/2013 | Cheng et al. | |
| 8,403,138 B2 | 3/2013 | Weisshaupt et al. | |
| 8,585,718 B2 | 11/2013 | Disch et al. | |
| 9,173,979 B2 | 11/2015 | Kelly et al. | |
| 9,259,514 B2 | 2/2016 | Andjelic et al. | |
| 9,358,008 B2 | 6/2016 | Mazzucco et al. | |
| 9,517,178 B2 | 12/2016 | Chancibot | |
| 9,883,866 B2 | 2/2018 | Roundy et al. | |
| D836,198 S | 12/2018 | Harris et al. | |
| 10,368,888 B2 | 8/2019 | Storz et al. | |
| D865,175 S | 10/2019 | Widenhouse et al. | |
| 11,051,814 B2 | 7/2021 | Roundy et al. | |
| 2002/0111641 A1 | 8/2002 | Peterson et al. | |
| 2004/0059378 A1 | 3/2004 | Peterson et al. | |
| 2004/0087985 A1 | 5/2004 | Loshakove et al. | |
| 2004/0138705 A1 | 7/2004 | Heino et al. | |
| 2004/0138765 A1 | 7/2004 | Bonissone et al. | |
| 2005/0107807 A1 | 5/2005 | Nakao | |
| 2005/0149064 A1 | 7/2005 | Peterson et al. | |
| 2005/0216036 A1 | 9/2005 | Nakao | |
| 2005/0277958 A1 * | 12/2005 | Levinson | A61B 17/122 606/139 |
| 2006/0124485 A1 | 6/2006 | Kennedy | |
| 2006/0217749 A1 * | 9/2006 | Wilson, Jr. | A61B 17/122 606/157 |
| 2007/0073314 A1 | 3/2007 | Gadberry et al. | |
| 2007/0208358 A1 | 9/2007 | Kayan | |
| 2008/0004637 A1 * | 1/2008 | Klassen | A61B 17/128 606/157 |
| 2008/0065154 A1 | 3/2008 | Allard et al. | |
| 2008/0103510 A1 | 5/2008 | Taylor et al. | |
| 2008/0312670 A1 | 12/2008 | Lutze et al. | |
| 2009/0030448 A1 | 1/2009 | Andre | |
| 2009/0072006 A1 | 3/2009 | Clauson et al. | |
| 2009/0152147 A1 | 6/2009 | Cannady | |
| 2009/0206144 A1 | 8/2009 | Doll et al. | |
| 2010/0010511 A1 | 1/2010 | Harris et al. | |
| 2010/0016875 A1 | 1/2010 | Nakao et al. | |
| 2010/0191262 A1 | 7/2010 | Harris et al. | |
| 2010/0191282 A1 | 7/2010 | Harris et al. | |
| 2010/0204717 A1 | 8/2010 | Knodel | |
| 2010/0312259 A1 | 12/2010 | Houser et al. | |
| 2011/0112551 A1 | 5/2011 | Adams et al. | |
| 2013/0144313 A1 * | 6/2013 | Hahn | A61B 17/128 606/142 |
| 2013/0172914 A1 | 7/2013 | Weisshaupt | |
| 2014/0128819 A1 | 5/2014 | Eaves | |
| 2014/0296884 A1 | 10/2014 | Motomura | |
| 2015/0080914 A1 | 3/2015 | Roundy et al. | |
| 2016/0120546 A1 * | 5/2016 | Roundy | A61B 17/1285 606/143 |
| 2018/0116669 A1 | 5/2018 | Roundy et al. | |
| 2021/0015486 A1 * | 1/2021 | Brodaczewski | A61B 17/1222 |
| 2021/0322010 A1 | 10/2021 | Roundy et al. | |
| 2021/0330328 A1 * | 10/2021 | Dreilinger | A61B 17/083 |

FOREIGN PATENT DOCUMENTS

| | | |
|---|---|---|
| CA | 2965986 C | 5/2019 |
| CN | 103989501 A | 8/2014 |
| CN | 103989501 B | 8/2014 |
| CN | 103989501 B | 3/2016 |
| CN | 107106182 B | 11/2019 |
| DE | 3204532 C2 | 12/1983 |
| DE | 19752331 C1 | 9/1999 |
| DE | 102006031092 B3 | 1/2008 |
| DE | 29720952 U1 | 5/2019 |
| EP | 0159453 | 10/1985 |
| EP | 0338754 | 10/1989 |
| EP | 0469524 | 2/1992 |
| EP | 0565892 | 10/1993 |
| EP | 1895917 | 3/2008 |
| EP | 1895917 B1 | 9/2008 |
| EP | 2456367 | 5/2012 |

(56) References Cited

FOREIGN PATENT DOCUMENTS

| | | |
|---|---|---|
| EP | 2701613 | 3/2014 |
| EP | 2456367 B1 | 9/2014 |
| EP | 2701613 B1 | 9/2016 |
| EP | 3113699 | 1/2017 |
| EP | 3113699 B1 | 8/2017 |
| JP | S58138447 A | 8/1983 |
| JP | H057593 A | 1/1993 |
| JP | 3124027 B2 | 1/2001 |
| JP | 2005530559 | 10/2005 |
| JP | 2017523810 A | 8/2017 |
| JP | 2017533042 A | 11/2017 |
| JP | 6532113 B2 | 5/2019 |
| KR | 101773205 B1 | 9/2017 |
| WO | WO1990010418 | 9/1990 |
| WO | WO2010118312 A2 | 10/2010 |
| WO | WO2011059666 | 5/2011 |
| WO | WO2012135735 | 10/2012 |
| WO | WO2015039024 A1 | 3/2015 |
| WO | WO2016073376 | 5/2016 |
| WO | WO2021214729 A1 | 10/2021 |

OTHER PUBLICATIONS

CN103989501B, Google Translation of CN103989501B, as early as Jun. 17, 2018, 11 pages.
CN103989501B, Google Translation of CN103989501B, as early as Feb. 21, 2020, 7 pages.
JP3124027, J-PlatPat Translation of JP3124027B, as early as Sep. 8, 2016, 6 pages.
JP3124027, Espacenet Translation of JP3124027B2, as early as Feb. 22, 2016, 6 pages.
JP2005/530559, Espacenet Translation of JP2005/530559, as early as Feb. 22, 2016, 30 pages.
JP2017523810A, Google Translation of JP2017523810A, as early as Feb. 21, 2020, 15 pages.
JPS58138447A, J-PlatPat Translation of JPS58138447A, as early as Jul. 10, 2018, 5 pages.
Patent Cooperation Treaty; International Preliminary Report on Patentability; International Search Report and Written Opinion of PCT/US2015/058669; dated May 9, 2017, 6 pages.
DE102006031092B3; "Google Machine Translation of DE102006031092B3"; as early as Mar. 20, 2020; 5 pages; Google translate.
Google Translate; Machine Translation of EP0159453A1; Google Patents, as early as Mar. 16, 2022; 7 pages.
Patent Cooperation Treaty; International Preliminary Report on Patentability for PCT/IB21/53384; dated Apr. 25, 2022; 3 pages.
Patent Cooperation Treaty; Corrected International Preliminary Report on Patentability for PCT/IB21/53384 with Annex comprising Article 34 amendments; dated Jun. 6, 2022; 54 pages.
DE29720952U1; "Patent Translate Powered by EPO and Google"; Machine-translation for DE29720952U1; as early as Aug. 18, 2021; 17 pages; Patent Translate; provided by PCT with ISR and WO.
Patent Cooperation Treaty; International Search Report and Written Opinion for PCT/IB21/53384; dated Aug. 18, 2021; 13 pages.
European Patent Office, "European Search Report including Supplementary European Search Report for EP15856303", dated Jun. 5, 2018, 8 pages.
Patent Cooperation Treaty, "International Preliminary Report on Patentability and Written Opinion of the International Searching Authority of PCT/US2014/055643", dated Mar. 22, 2016, 6 pages.
Patent Cooperation Treaty, "International Search Report and Written Opinion of the International Searching Authority of PCT/US2014/055643", dated Dec. 29, 2014, 9 pages.
Patent Cooperation Treaty, "International Search Report and Written Opinion of the International Searching Authority of PCT/US2015/058669", dated Feb. 1, 2016, 11 pages.

\* cited by examiner

FIG. 16
FIG. 17
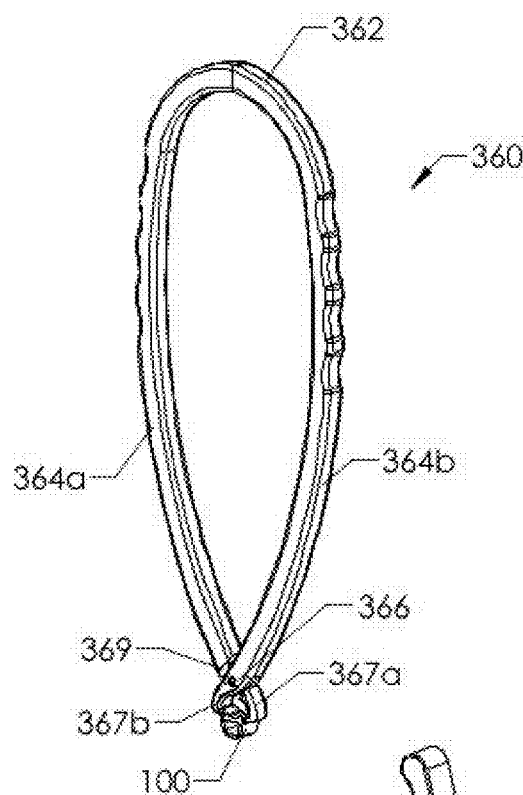
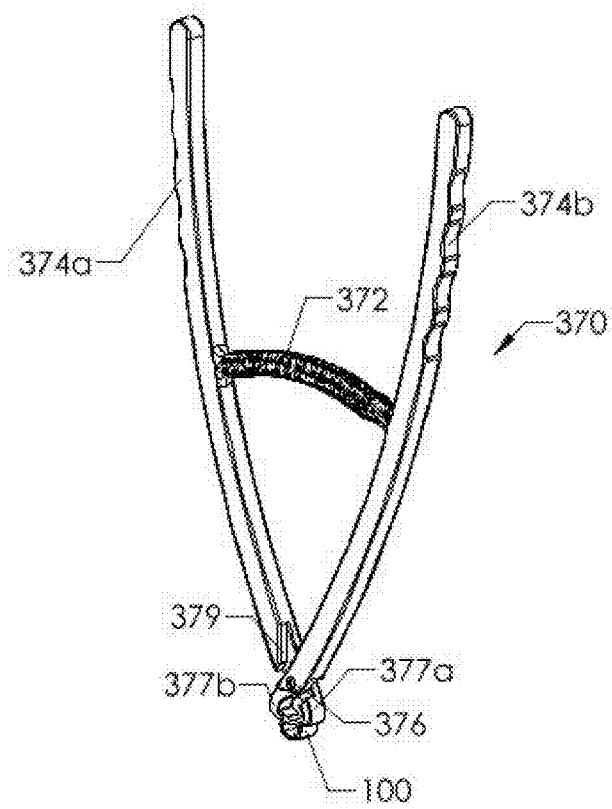
FIG. 18
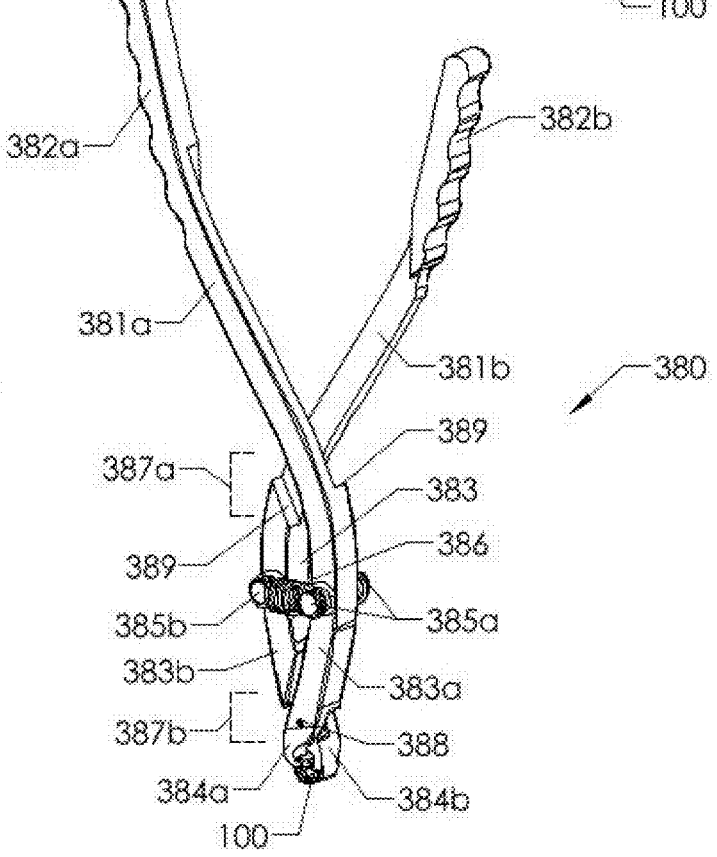

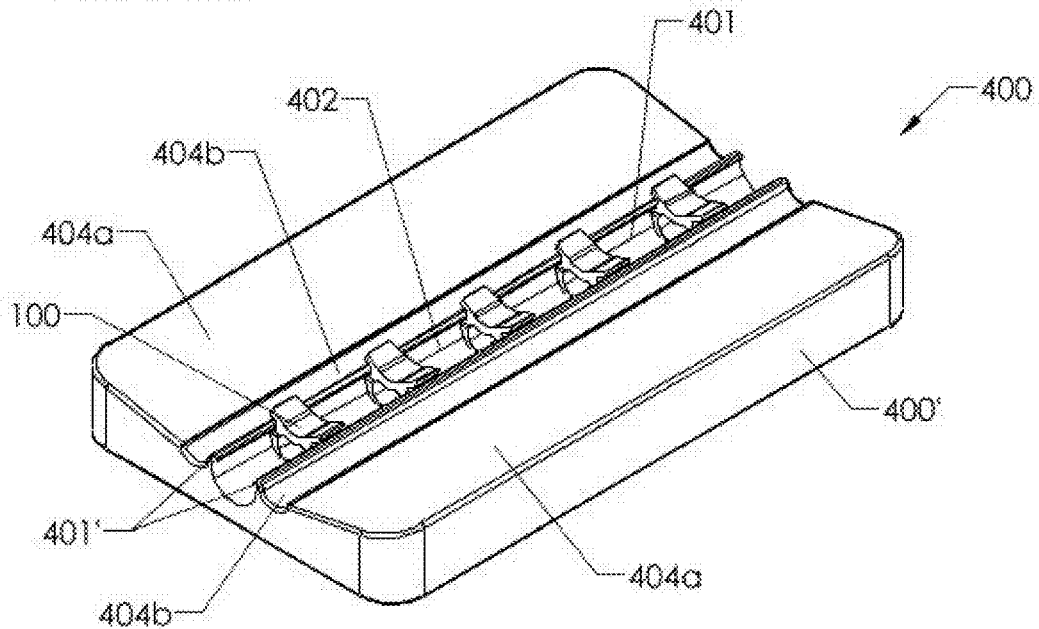
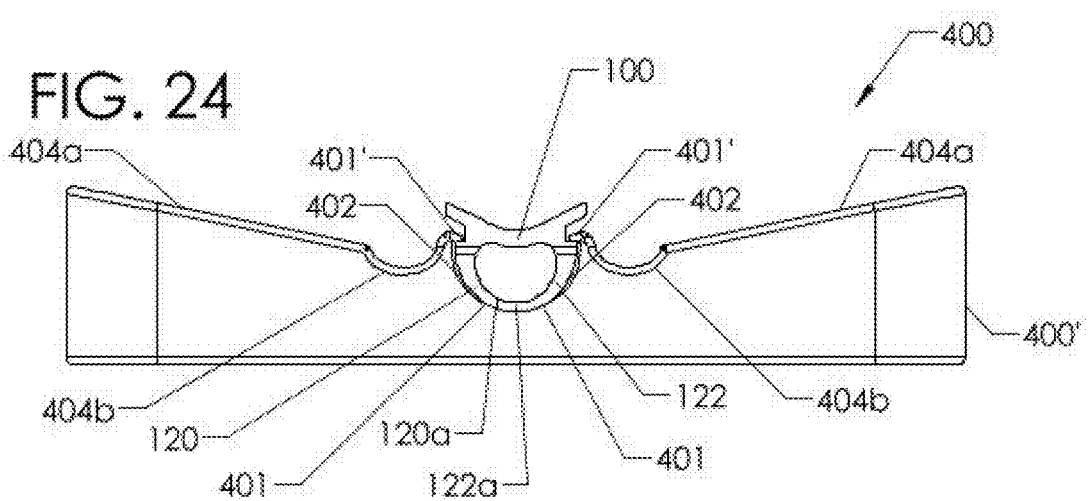
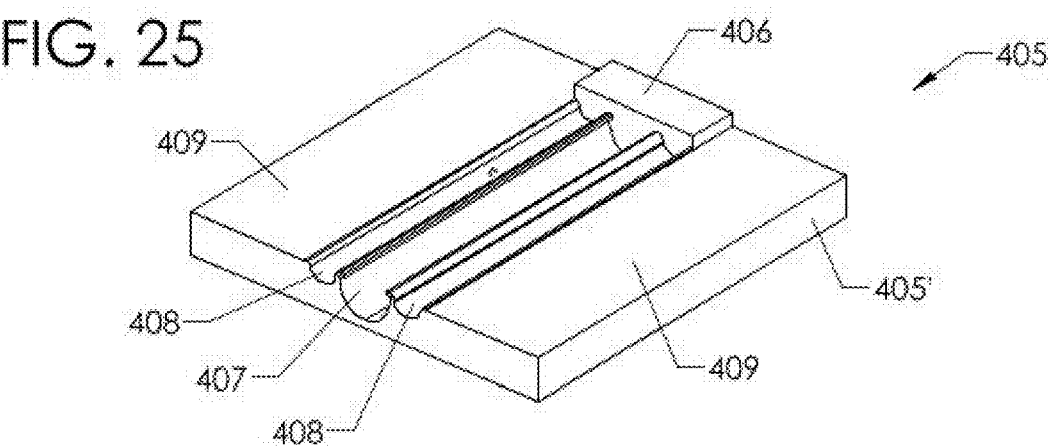

FIG. 37
FIG. 38
FIG. 39
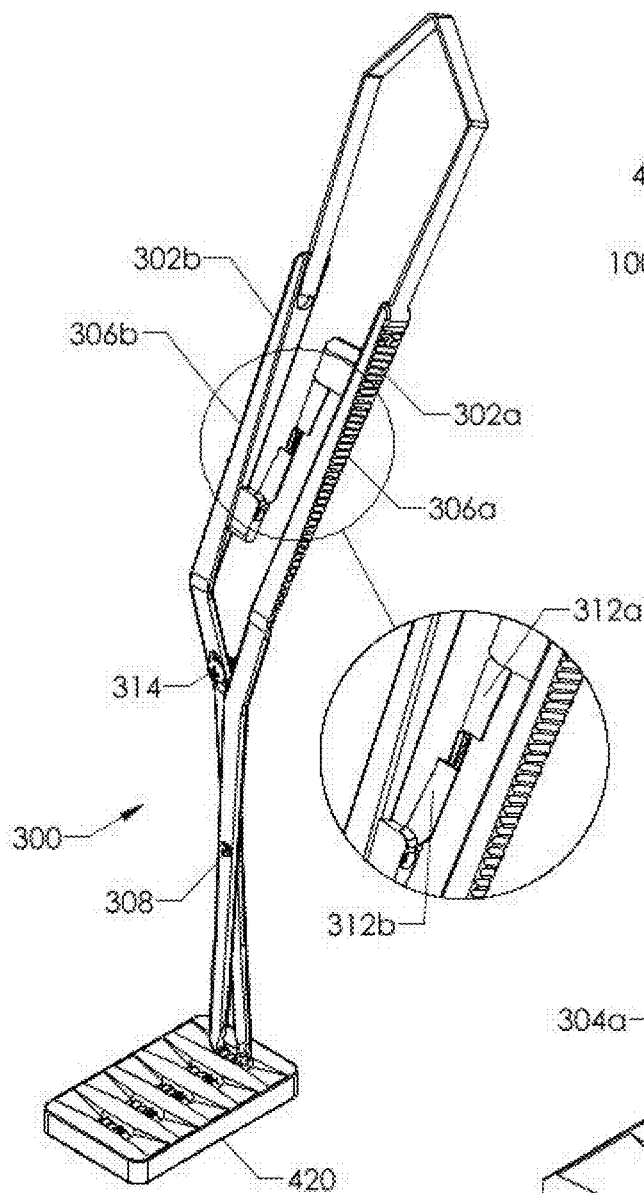
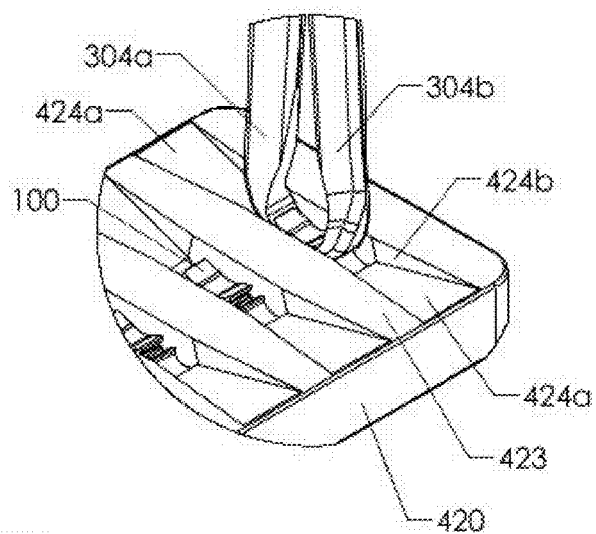
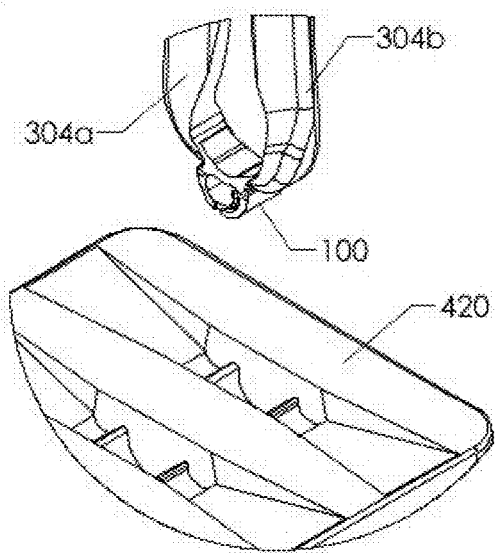

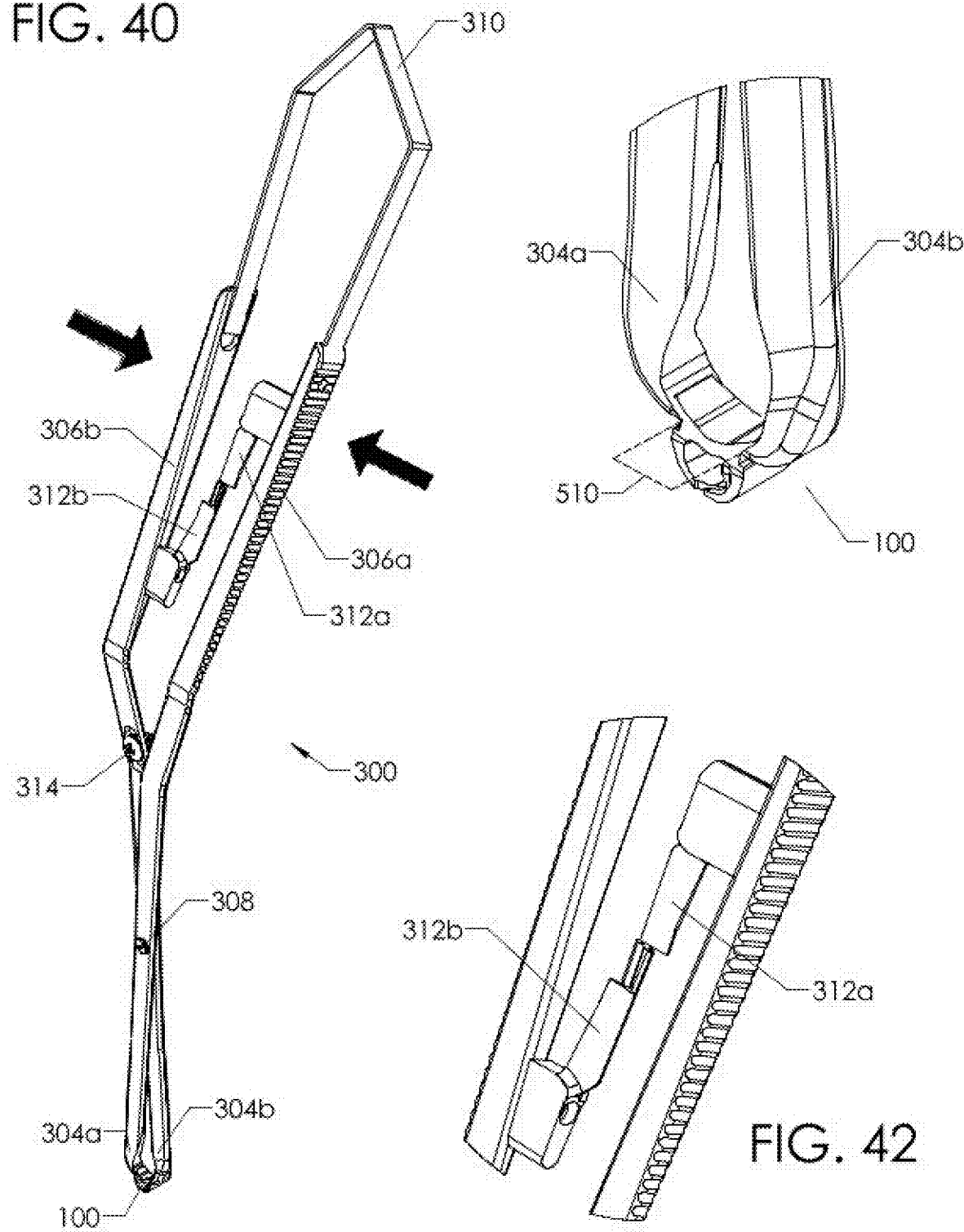

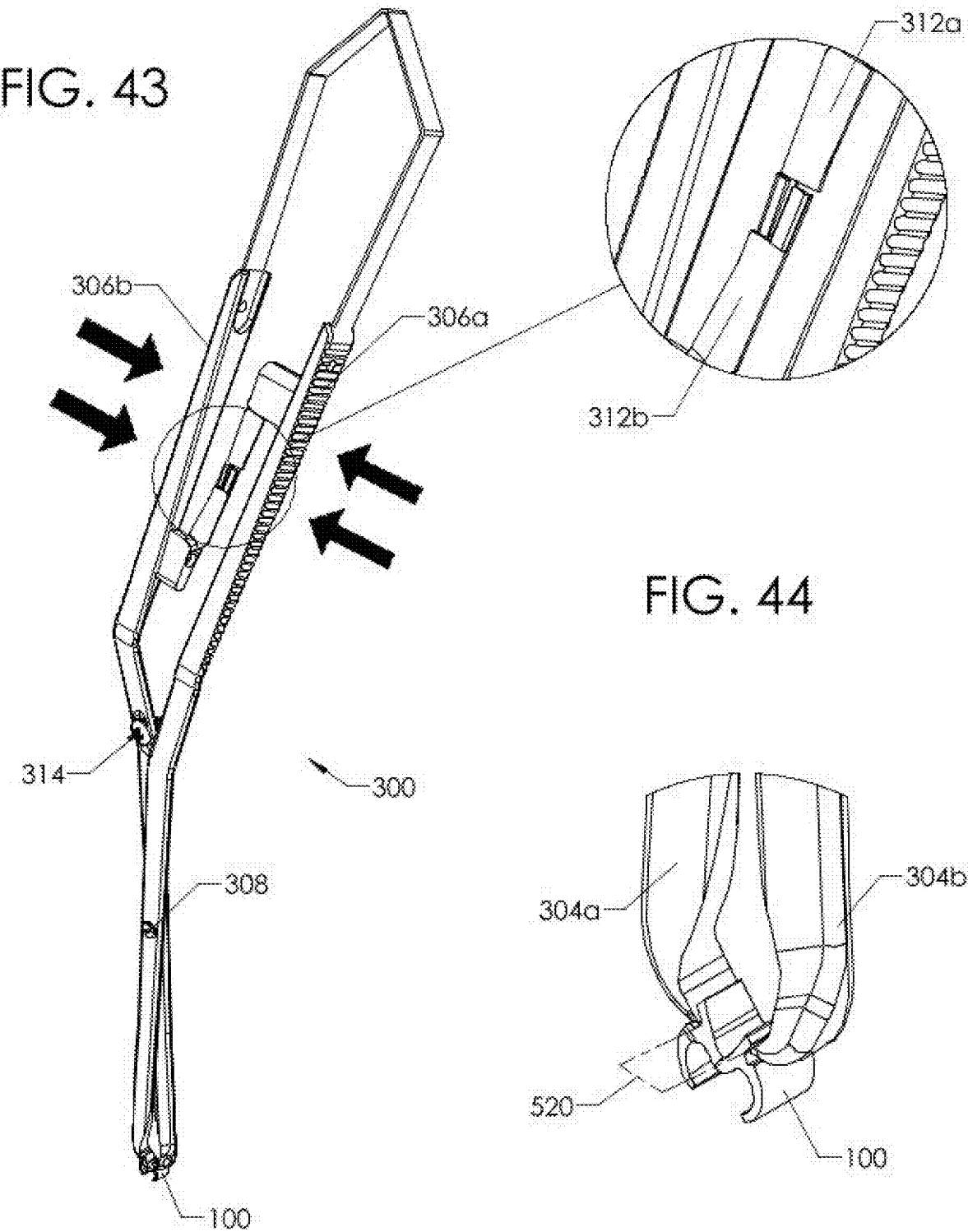
FIG. 43
FIG. 44
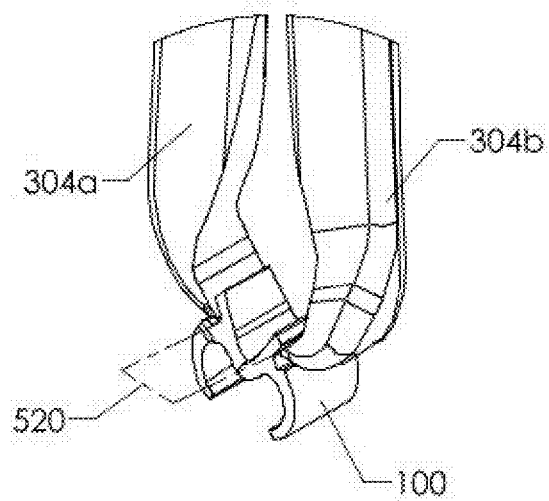

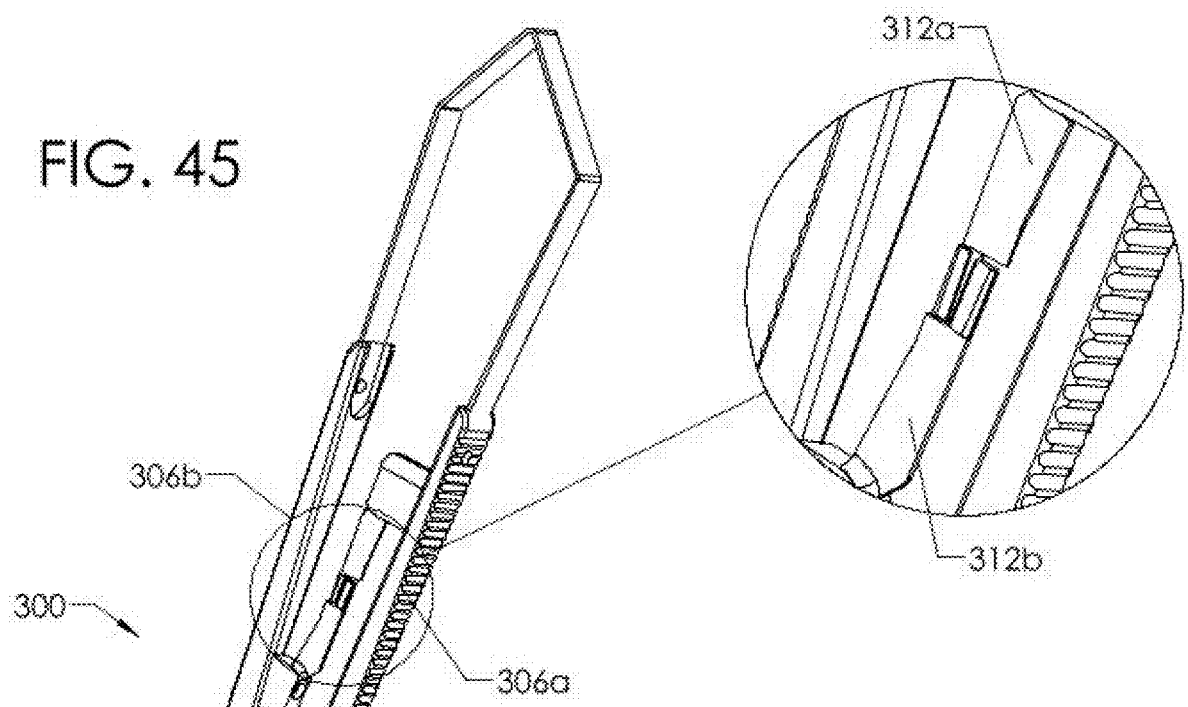
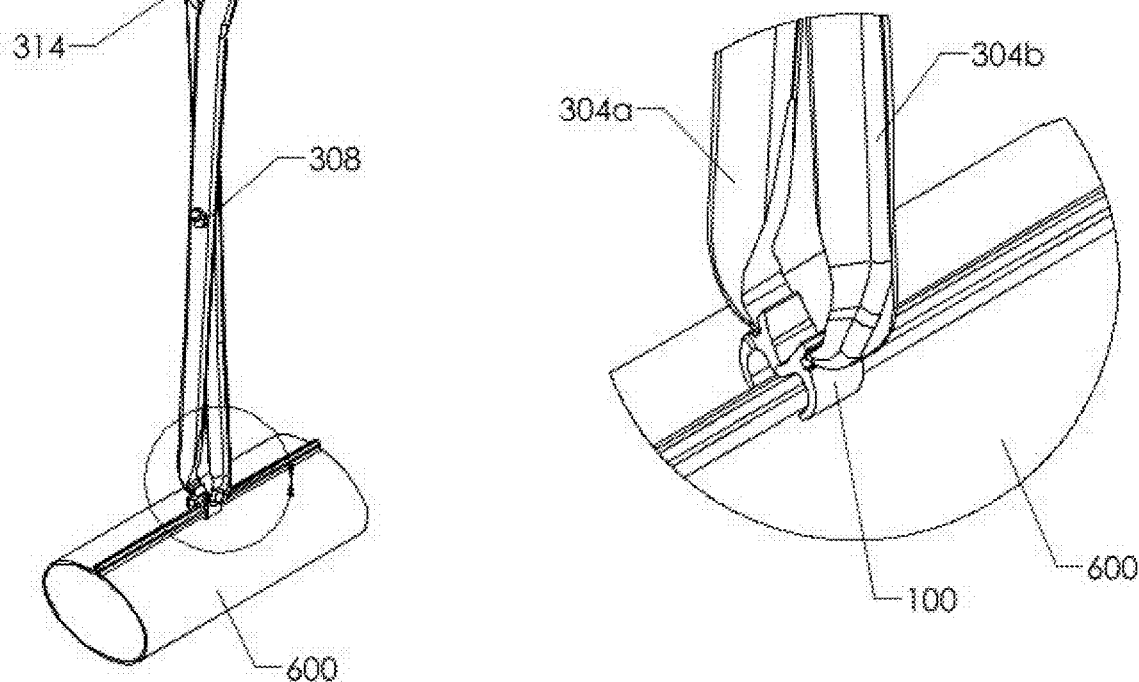

CLIPS, APPLIERS, AND CARTRIDGES

GOVERNMENT SUPPORT CLAUSE

This invention was made with government support under NS107104 awarded by the National Institutes of Health, and 1648203 awarded by the National Science Foundation. The government has certain rights in the invention.

STATEMENT REGARDING FEDERALLY SPONSORED RESEARCH OR DEVELOPMENT

This invention was made with Government support under a Small Business Innovation Research Program Phase I grant (Federal Award Identification Number: 1648203) awarded by the National Science Foundation. The Government has certain rights in this invention.

This invention was made with government support under a Small Business Innovation Research Program Phase II grant (Federal Award Identification Number: R44NS107104) awarded by the National Institutes of Health. The government has certain rights in the invention.

COPYRIGHT NOTICE

A portion of the disclosure of this patent document contains material that is subject to copyright protection. The copyright owner has no objection to the facsimile reproduction of the patent disclosure as it appears in the Patent and Trademark Office patent files or records, but otherwise reserves all copyright rights whatsoever.

BACKGROUND

The present disclosure describes apparatuses, methods, and/or systems that generally relate to the technical field of surgical clips, appliers, and cartridges, and specifically relate to the technical field of surgical tissue closure.

Tissue (e.g. human tissue) may be intentionally or inadvertently opened. For example, during spinal surgery, the dura mater (the tough outer membrane covering the brain and spinal cord) may be intentionally opened (e.g. dural incision or durotomy) or it may be opened inadvertently (e.g. incidental durotomy or dural opening). Openings in tissue ultimately need to be closed by, for example, suturing, stapling, or clipping. Some of the earliest closure procedures used sutures (or stitches). While the use of staples was pioneered as early as the early 1900s, it wasn't until at least the 1950s that staples became commercially viable. In the 1990s, clips began to replace staples for some applications. U.S. Pat. No. 9,883,866, U.S. Patent Application Publication No. 2015/0080914, and U.S. Patent Application Publication No. 2018/0116669, all to Roundy et al., disclose various types of clips and appliers for tissue closure. In the broadest sense, surgical clips are used to join tissue during medical procedures. Surgical clips may be used, for example, to close dural openings.

Minimally invasive surgery (MIS) is becoming more commonly used during surgical procedures because it results in less tissue disruption than traditional procedures. Minimally invasive surgeries may be used to treat a variety of medical indications including, but not limited to, herniated discs, spinal stenosis, synovial cysts, spondylolisthesis, deformity, and intradural tumors. Such procedures use smaller incisions (and smaller ports) to decrease intraoperative blood loss, reduce tissue disruption, decrease postoperative pain, and decrease lengths of hospital stays, for example.

Minimally invasive surgery makes use of smaller ports and thus has more confined working areas. Due to the physical limitations of confined working areas, closing tissue through small incisions and/or ports may be technically difficult and/or time-consuming. For example, if a durotomy occurs during minimally invasive spine surgery, the ability to close the durotomy using conventional suture and knot-tying techniques may be compromised (e.g. the suture material cannot be manipulated sufficiently to achieve tight closure). Using staples can also be problematic and require significant numbers of staples (e.g. the staples must be placed sufficiently close together along a dural opening in order to close the tissue since such staples may be too narrow to cover and hold significant lengths along the tissue break). Additionally, staples are penetrating in that they penetrate the tissue that can lead to fluid leakage in the dura.

SUMMARY

The present disclosure describes apparatuses, methods, and/or systems that generally relate to the technical field of surgical clips, appliers (also referred to as applicators), and cartridges, and specifically relate to the technical field of surgical tissue closure.

Disclosed herein is a medical device forming method, the method comprising the steps of: (a) receiving a no more than partially cured rubbery device with a gap defined therein; (b) placing the no more than partially cured rubbery device in a form such that the gap is closed; and (c) curing the no more than partially cured rubbery device such that it becomes a flexible but rigid device.

Some preferred medical device forming methods may include the step of receiving the no more than partially cured rubbery device may include the step of using a partial thermal injection molding process to create a no more than partially cured rubbery device with a gap defined therein. For other preferred medical device forming methods, the step of receiving the no more than partially cured rubbery device may include the step of using a partial thermal injection molding process to create a no more than partially cured rubbery device with a gap defined therein that comprises the steps of: (a) injecting fluid clip material into a mold; (b) subjecting the clip material in the mold to a process; and (c) removing the clip material from the mold before the clip material has crystallized. For still other preferred medical device forming methods, the step of curing the partially cured rubbery device may include the step of causing the partially cured rubbery device to crystallize or anneal. And for other preferred medical device forming methods, the step of curing the partially cured rubbery device may include the step of heating the partially cured rubbery device. Finally, for other preferred medical device forming methods, the gap in the flexible but rigid device may be opened and closed. Some preferred medical device forming methods may include more than one of these additional features.

Disclosed herein is an applier for manipulating clips that includes a first shaft, a second shaft, a securing pivot, and an engageable and disengageable lock. The first shaft has a first pinching tip at least substantially at a first shaft tip end, a first handle at least substantially at a first shaft handle end, and a first shaft midpoint between the first shaft tip end and the first shaft handle end. The second shaft has a second pinching tip at least substantially at a second shaft tip end, a second handle at least substantially at a second shaft handle end, and a second shaft midpoint between the second shaft tip end and second shaft the handle end. The securing pivot pivotally connects the first shaft and the second shaft at the first shaft midpoint and the second shaft midpoint. The engageable and disengageable lock substantially preventing the handles from spreading when the lock is engaged. The applier has at least three stages, including: (i) an un-pinched stage in which the first pinching tip is relatively far from the second pinching tip, the first handle is relatively far from the second handle, and the lock is unengaged; (ii) a pinched stage in which the first pinching tip is relatively close to the second pinching tip, the first handle is relatively close to the second handle, and the lock is unengaged; and (iii) a partially-pinched stage in which the first pinching tip is at an in-between distance from the second pinching tip, the first handle is at an in-between distance from the second handle, and the lock is engaged.

For some preferred appliers the pinching tip is an inwardly-angled pinching tip. Other preferred appliers may include an expander for encouraging increasing distance between the handle of a first shaft and the handle of a second shaft. Still other preferred appliers the engageable and disengageable lock may be a two-part lock in which a first lock part associated with the first shaft and a second lock part associated with the second shaft. Some preferred appliers may include more than one of these additional features.

Disclosed herein is a cartridge for holding clips, the cartridge comprising: (a) a cartridge body; (b) at least one formation well defined within the body; and (c) each the at least one formation well sized and shaped to hold at least one of the clips in the closed position with the teeth of opposing sides touching.

For some preferred cartridges the at least one formation well may be a single elongated channel formation well sized and shaped to hold a plurality of the clips in the closed position with the teeth of opposing sides touching. For other preferred cartridges the at least one formation well may be a plurality of individual formation wells, each individual formation well sized and shaped to hold a single one of the clips in the closed position with the teeth of opposing sides touching. Still other preferred cartridges may have formation structure in the at least one formation well, the formation structure being, for example, at least one formation pin or at least one formation finger. Yet other preferred cartridges may include guide structure to assist appliers in removing the clips from the formation wells, the guide structure being, for example, angled surfaces, side channels, and/or wall guides. Some preferred cartridges may include more than one of these additional features.

Disclosed herein is an applier for manipulating clips, the appliers including a first shaft, a second shaft, a securing pivot, and a limiter. The first shaft preferably has a first pinching tip at least substantially at a first shaft tip end, a first handle at least substantially at a first shaft handle end, and a first shaft midpoint between the first shaft tip end and the first shaft handle end. The second shaft preferably has a second pinching tip at least substantially at a second shaft tip end, a second handle at least substantially at a second shaft handle end, and a second shaft midpoint between the second shaft tip end and second shaft the handle end. The securing pivot pivotally preferably connecting the first shaft and the second shaft at the first shaft midpoint and the second shaft midpoint. The limiter preferably for limiting the distance between the first pinching tip and the second pinching tip. For some preferred appliers the first shaft preferably has a first bent central shaft portion and the second shaft prefer- ably has a second bent central shaft portion, and when the first shaft and the second shaft overlap, the first bent central shaft portion and the second bent central shaft portion define a central opening therebetween.

Objectives, features, combinations, and advantages described and implied herein will be more readily understood upon consideration of the following detailed description of the invention, taken in conjunction with the accompanying drawings. The subject matter described herein is also particularly pointed out and distinctly claimed in the concluding portion of this specification.

DESCRIPTION OF THE DRAWINGS

The accompanying drawings illustrate various exemplary apparatuses, and/or systems related to surgical clips, appliers, and cartridges used for surgical tissue closure, and/or provide teachings by which the various exemplary surgical clips, appliers, and cartridges and the methods related thereto are more readily understood.

FIG. 16 is a perspective view of a first alternative applier.

FIG. 17 is a perspective view of a second alternative applier.

FIG. 18 is a perspective view of a third alternative applier.

FIG. 23 is a perspective view of an exemplary cartridge with a single elongated channel formation well and angled upper surfaces and side channels.

FIG. 24 is an end view of the exemplary cartridge of FIG. 23.

FIG. 25 is a perspective view of an exemplary cartridge similar to the exemplary cartridge of FIG. 23, but with blocking structure at one end of a single elongated channel formation well and a flat upper surface.

FIG. 37 is a perspective view of the applier in the partially-pinched stage beginning to lift a clip from a cartridge.

FIG. 38 is a perspective detailed view of the applier pinching tips of FIG. 37 beginning to remove one clip.

FIG. 39 is a perspective detailed view of the applier in the partially-pinched stage lifting the clip from the cartridge.

FIG. 40 is a perspective view of the applier showing a "medium" amount of inward pressure applied to the handles to put the applier in the partially-pinched stage.

FIG. 41 is a perspective detailed view of the pinching tips of the applier after the application of the "medium" amount of inward pressure to engage the clip grooves.

FIG. 42 is a perspective detailed view of the first lock part of the exemplary lock engaged with the second lock part of the exemplary lock.

FIG. 43 is a perspective view of the applier showing a "maximum" amount of inward pressure applied to the handles to put the applier in the pinched stage.

FIG. 44 is a perspective detailed view of the pinching tips of the applier after the application of the "maximum" amount of inward pressure that causes the clip to spread to the open position.

FIG. 45 is a perspective view of the applier in the pinched stage applying a clip to close tissue.

FIG. 46 is a perspective detailed view of the pinching tips in the pinched stage applying a clip to close tissue.

Figure 1A:
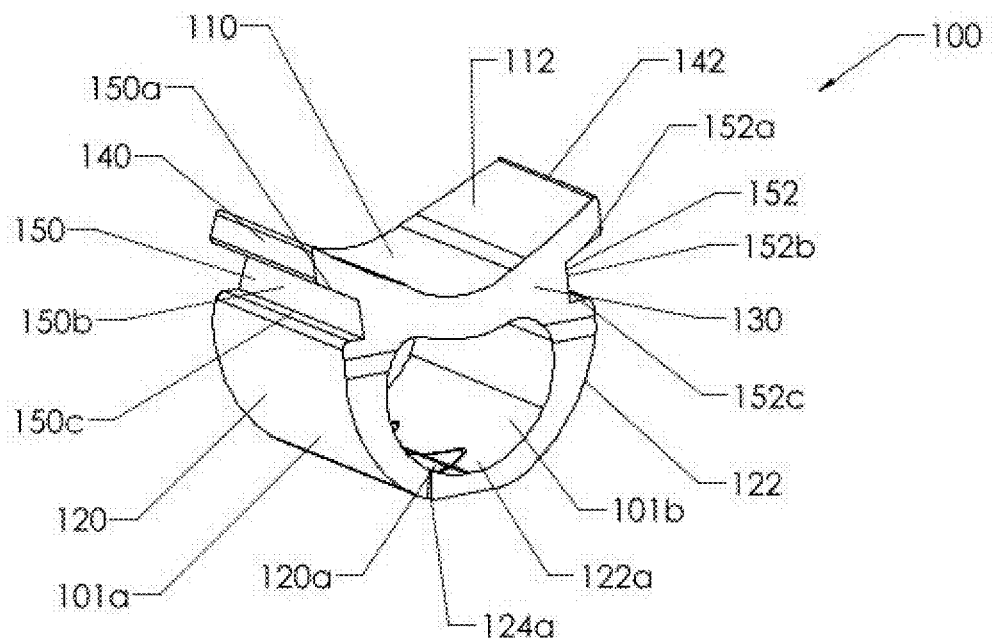
FIG. 1A is a front face perspective view of an exemplary clip in a closed position.

The drawing figures are not necessarily to scale. Certain features or components herein may be shown in somewhat schematic form and some details of conventional elements may not be shown or described in the interest of clarity and conciseness. The drawing figures are hereby incorporated in and constitute a part of this specification.

DETAILED DESCRIPTION

Figure 1B:
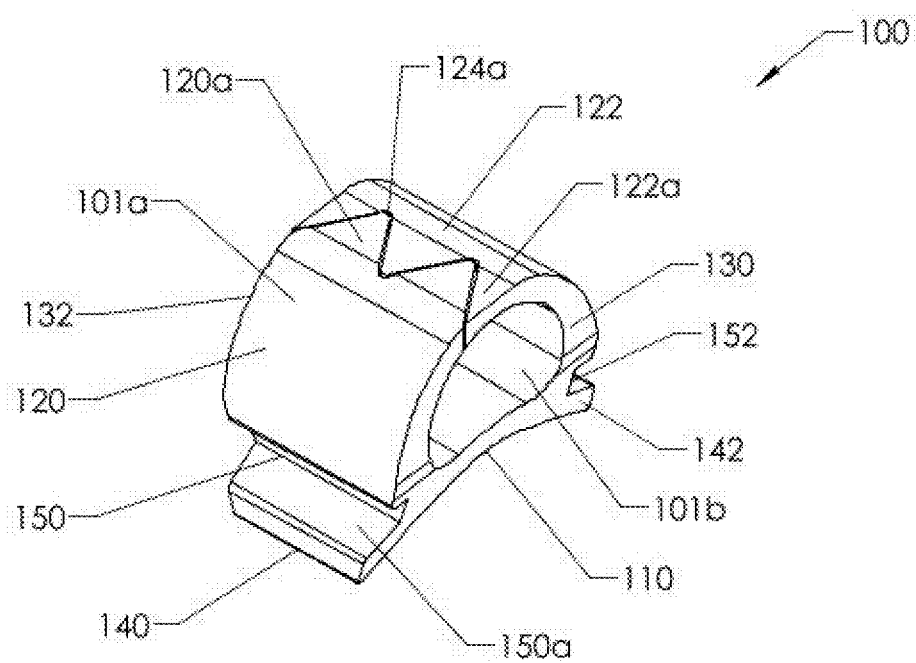
FIG. 1B is a bottom side perspective view of the exemplary clip of FIG. 1A in the closed position.

The present disclosure describes apparatuses, methods, and/or systems that generally relate to surgical clips (clips), surgical appliers (appliers), and surgical cartridges (cartridges) for storing the clips until they are removed by an applier. An exemplary clip 100 is shown in FIGS. 1A-1B (closed position) and FIGS. 2A-2B (open position). FIGS. 3-9 are used to illustrate exemplary apparatuses and processes of creating the surgical clips. Exemplary preferred appliers are shown in FIGS. 10-15. Alternative exemplary preferred appliers are shown in FIGS. 16-22. An exemplary preferred cartridge is shown in FIGS. 23-24. Alternative exemplary preferred cartridges are shown in FIGS. 25-35. FIGS. 36-50 show various combinations of interactions between clips, appliers, cartridges, and/or tissue.

Exemplary clips, appliers, cartridges, and methods and systems associated therewith may be better understood with reference to the drawings, but these are not intended to be of a limiting nature. The same reference numbers will be used throughout the drawings and description in this document to refer to the same or like parts. The shown shapes and relative dimensions are preferred, but are not meant to be limiting unless specifically claimed, in which case they may limit the scope of that particular claim.

Clips

Figure 2A:
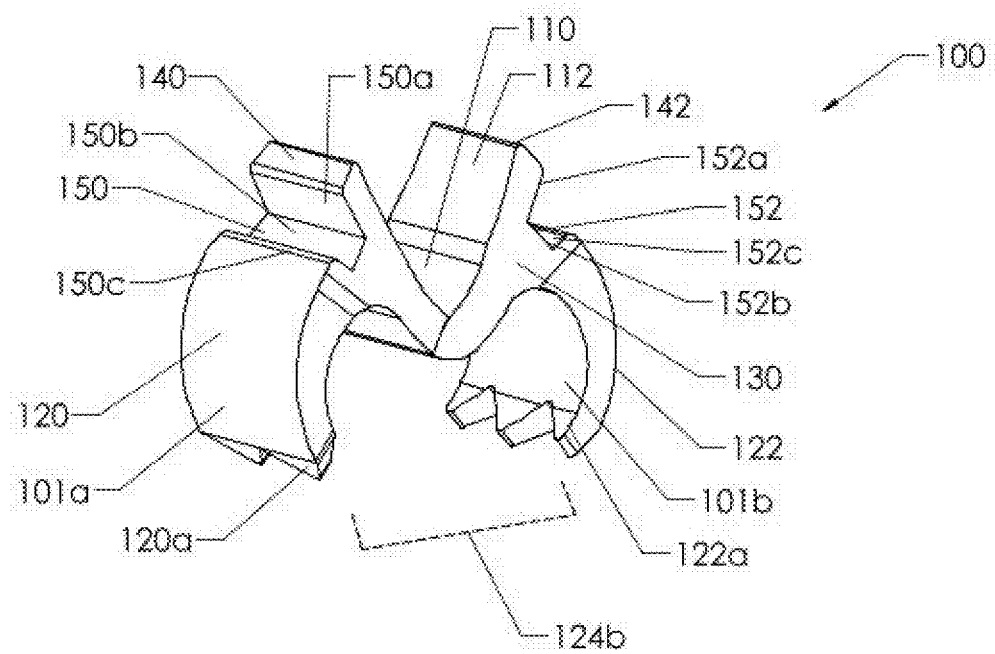
FIG. 2A is a front face perspective view of an exemplary clip in an open position.
Figure 2B:
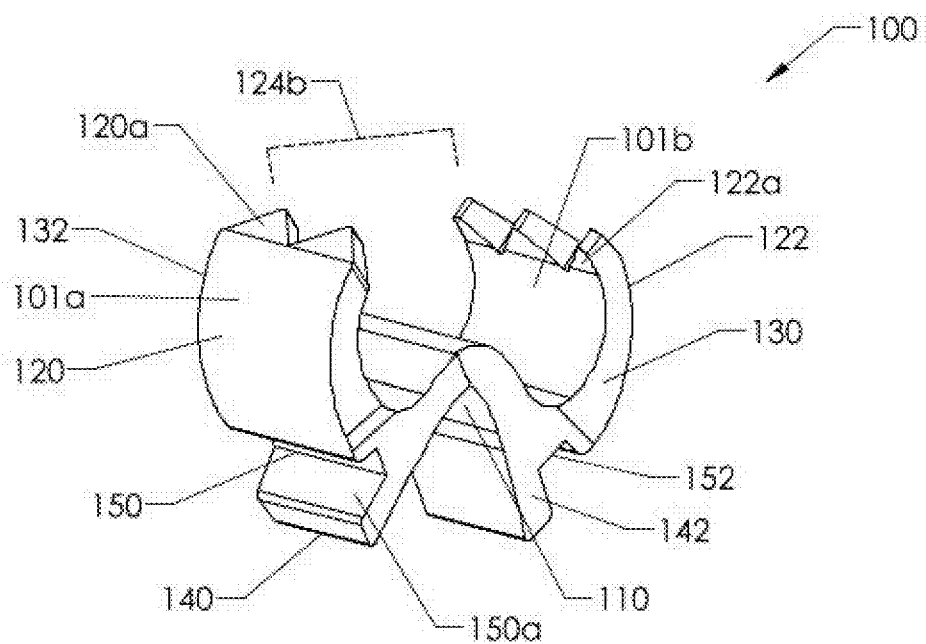
FIG. 2B is a bottom side perspective view of the exemplary clip of FIG. 2A in the open position.

As shown in FIGS. 1A-1B and FIGS. 2A-2B, an exemplary surgical clip 100 has an exterior surface 101a and an interior surface 101b. The clip 100 has a top portion 110 with an upper surface 112. Extending downwardly from the top portion 110 are opposing sides 120 and 122 (shown as inwardly curved sides) that terminate in "teeth" 120a and 122a that together form a gripping "mouth." FIGS. 1A-1B show the clip 100 in a closed position in which the teeth 120a and 122a essentially touch (although there technically is still a closed or touching gap 124a therebetween as the teeth 120a and 122a are not melded together). Because of limitations of drawing preparation, some clips 100 described as being in the closed position are shown in some of the figures (e.g. FIGS. 26A, 26B, 32-34, 41) with a slight gap between teeth 120a and 122a, but would actually only have a touching gap 124a therebetween. In some figures (e.g. FIGS. 47-50), the size of the gap is determined by the thickness of the tissue between the teeth 120a and 122a, but the clip 100 is described as being in the closed position because there would only be a touching gap 124a if the tissue was not between the teeth 120a and 122a. FIGS. 2A-2B show the clip 100 in an open position in which the teeth 120a and 122a are distal from each other (shown as an open or spread gap 124b). The clip may be in the open position because it is held apart by the use of an applier. A clip 100 in an open position is shown, for example, in FIG. 44.

The top portion 110 and sides 120 and 122 have opposing faces 130 and 132. The top portion 110 also has two opposing wings 140 and 142. When the clip 100 is oriented with the top portion 110 at the top (as shown in FIGS. 1A and 2A), the first side 120 and the second side 122 are located below the first wing 140 and the second wing 142, respectively. Grooves 150 and 152 are formed on the exterior surface 101a of the clip 100 such that the first groove 150 is between the top portion of the first side 120 and the bottom portion of the overhanging portion of the first wing 140 and the second groove 152 is between the top portion of the second side 122 and the bottom portion of the overhanging portion of the second wing 142. Put another way, the shown grooves 150 and 152 have an "overhang" 150a and 152a, a "wall" 150b and 152b, and a "floor" (or shoulder) 150c and 152c. The shown angles between the various portions of the grooves 150 and 152 may be adjusted for use with a specific applier.

FIGS. 3-8 show clip forming tools (forms 200, 220, 240) that may be used to create clips 100 (a single clip 100 is shown in the bottom left clip form well of the forms). (Cartridges 400, 405, 410, 418, 420, 440, 450, 460, 470, 480, which will be discussed below, can also be used to create clips 100.) These forms, as will be discussed, are used in a unique forming step after "rubbery" clips are created (e.g. using thermal injection molding). FIG. 9 shows a flow chart of an exemplary process for using the forms 200, 220, 240 to create clips 100.

There are many conventional processes used to manufacture medical devices from polymers and/or co-polymers. One conventional process used to manufacture medical devices is thermal injection molding. A traditional thermal injection molding process injects fluid (e.g. melted) material into a mold, subjects the material in the mold to a process, and removes (e.g. ejects) the device from the mold when the process is "complete." (Exemplary thermal injection molding processes are discussed in U.S. Pat. No. 4,744,365 to Kaplan et al., U.S. Pat. No. 9,173,979 to Kelly, and U.S. Pat. No. 9,259,514 to Andjelic et al.) Thermal injection molding, however, may result in molded parts that have inferior properties if the devices do not properly crystallize or anneal after molding (which can be referred to as a "crystallizing problem"). Improperly crystallized devices (e.g. devices that have not gone through or only partially gone through the final heating step of the thermal injection molding process) tend to be "rubbery" and are not suitable for use as a clip. U.S. Pat. No. 9,173,979 to Kelly et al. identified problems associated with crystallizing. Another problem with conventional processes used to manufacture medical devices can be described as an "unwanted gap" problem. Because the entire process is performed in the mold, a medical device such as the clip would have to have a slight gap (created by a wall or barrier of the mold) between the forming teeth. If the clip hardened in the mold, the result would be a clip with a slight gap between the teeth 120a and 122a that would be present even when the clip was in the closed position. Put another way, there would be a space (slight gap) formed between the teeth. This space (slight gap) would be undesirable because the finished clip would never fully close. If no wall or barrier was present in the mold, the teeth 120a and 122a would be touching and would meld together. Put another way, the fluid material that would form the opposing sides 120 and 122 would form a complete loop. This is also undesirable.

The medical device (e.g. clip) forming process described herein may be used to manufacture medical devices from clip material such as polymers and/or co-polymers. Exemplary clip materials include, but are not limited to polylactic acid (PLA), poly(p-dioxanone) (PDO), polyglycolic acid (PGA), polycaprolactone (PCL), and copolymers of lactide, glycolide, p-dioxanone, trimethylene carbonate, ε-caprolactone, in various combinations. The clip material used is preferably bioabsorbable, although alternative clip material may not be bioabsorbable.

The process described herein that is used to manufacture medical devices is preferably an at least partial thermal injection molding process (which, for purposes of this description could include thermal forming processes such as injection molding (including plastic injection molding), solvent casting, extrusion, and combinations thereof). Fluid clip material (which may be clip material that is heated to a viscosity in which is can readily flow into the mold) is injected into a mold. The clip material inside the mold does not go through or only partially goes through the final heating step of the thermal injection molding process so that the clip material is "improperly crystallized" to a "rubbery" state. The term "rubbery" is meant to describe a texture similar to gelatin or a gummy worm such that, although formed completely, a clip in the "rubbery" phase can be described as floppy, flexible, soft, and/or squishy.) Another way to describe the term, "rubbery" is that it is an "amorphous" solid (as opposed to "crystalline" or "crystallized" solid). In an amorphous solid, the molecules line up randomly. In a crystallized solid, the molecules line up in a regular pattern. The system described herein advantageously uses the rubbery phase created crystallizing problem.

If the thermal injection molding process does not complete (crystallizing or annealing is no more than partial, which can be described as no more than partially cured), but only gets to the "rubbery" phase, a clip forming process as described herein may include an additional "forming step" in which the clip 100 is held in a form 200, 220, or 240 (or, as will be discussed later, a cartridge) with the teeth 120a and 122a touching. Significantly, because the clip 100 is no more than partially cured, even though the teeth 120a and 122a are touching, the teeth 120a and 122a do not meld together. Heating (or otherwise treating or curing) the clips in the form 200, 220, or 240 expedites the final curing and crystallization of the clips. This can be thought of as "annealing" in the form such that the clips, which are held in their correct shape (closed position), are allowed to crystallize (or the polymer molecules align giving the clips different material properties).

When removed from the form 200, 220, or 240, the now cured clip 100 is more rigid, but still flexible, such that the clip 100 can be held in an open position (opened), but return to and maintain the closed position (closed). The characteristic of a clip that has been open being able to return to the closed position (or "as molded" or "original") can be described as "return" or "shape memory." (Return or shape memory is not limitless. If a clip is opened too far (over-opening), it may experience "plastic deformation" in which the clip may deform permanently and not be able to return to the closed position.) When the clip 100 is opened (see FIGS. 2A and 2B), the top portion 110 (which acts as a spring hinge—bending but providing some resistance) bends so that the sides 120 and 122 and the teeth 120a and 122a move away from each other. In the closed position (see FIGS. 1A and 1B), the teeth 120a and 122a are preferably touching (or, when in use, held apart by tissue therebetween). The result is a clip 100 that can be opened and closed and, when in the closed position, can securely grip tissue between the teeth 120a and 122a.

Figure 3:
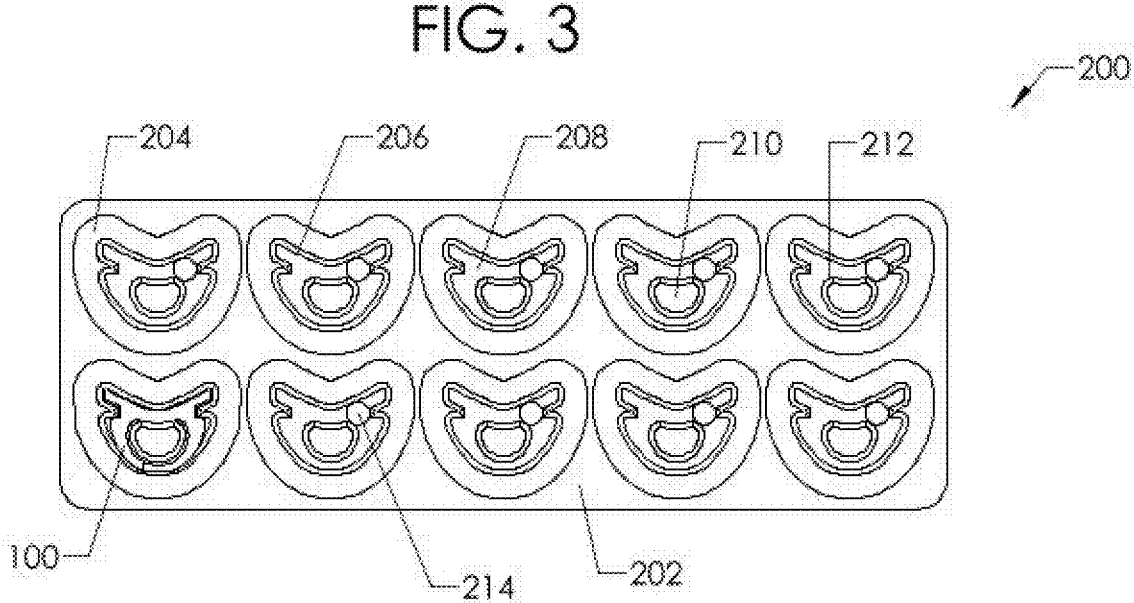
FIG. 3 is a top plan view of a first exemplary form for creating clips described herein.
Figure 4:
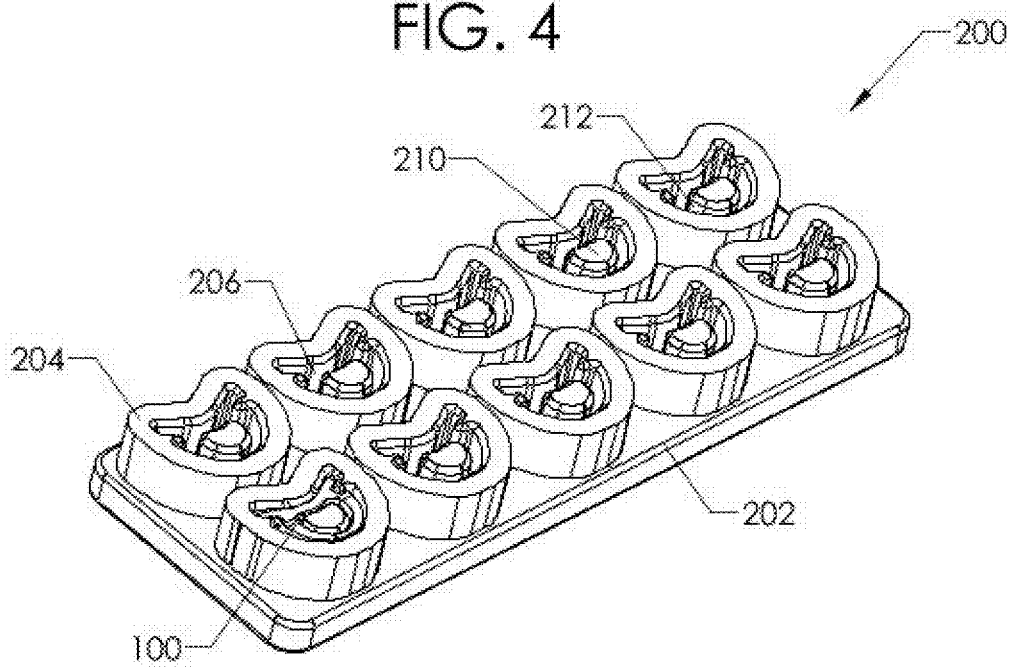
FIG. 4 is a top perspective view of the first exemplary form of FIG. 3.

FIGS. 3 and 4 show a first exemplary form 200 for use in manufacturing or creating clips (including clips 100). The shown first exemplary form 200 includes a field 202 with a plurality of clip form wells 204. Each clip form well 204 has an interior wall 206 that is preferably substantially coextensive with at least the majority of the exterior surface 101a of the clip 100 (e.g. the top portion 110 and the opposing sides 120 and 122 but not the faces 130 and 132). Each clip form well 204 also has a back surface 208 (that may be contiguous with the field 202) that is preferably substantially coextensive with at least the majority of one of the faces 130 and 132 of a clip 100 positioned in a clip form well 204. Each clip form well 204 of the first exemplary form 200 is shown as having a central protrusion 210 that projects from the back surface 208 and an exterior wall 212 that is preferably substantially coextensive with at least the majority of the interior surface 101b of the clip 100 (the interior surface 101b of the clip 100 includes the surfaces of the opposing sides 120 and 122 that face each other). The back surface 208 may also have an aperture 214 that may be used to assist in the removal of the clip 100 from the clip form well 204.

Figure 5:
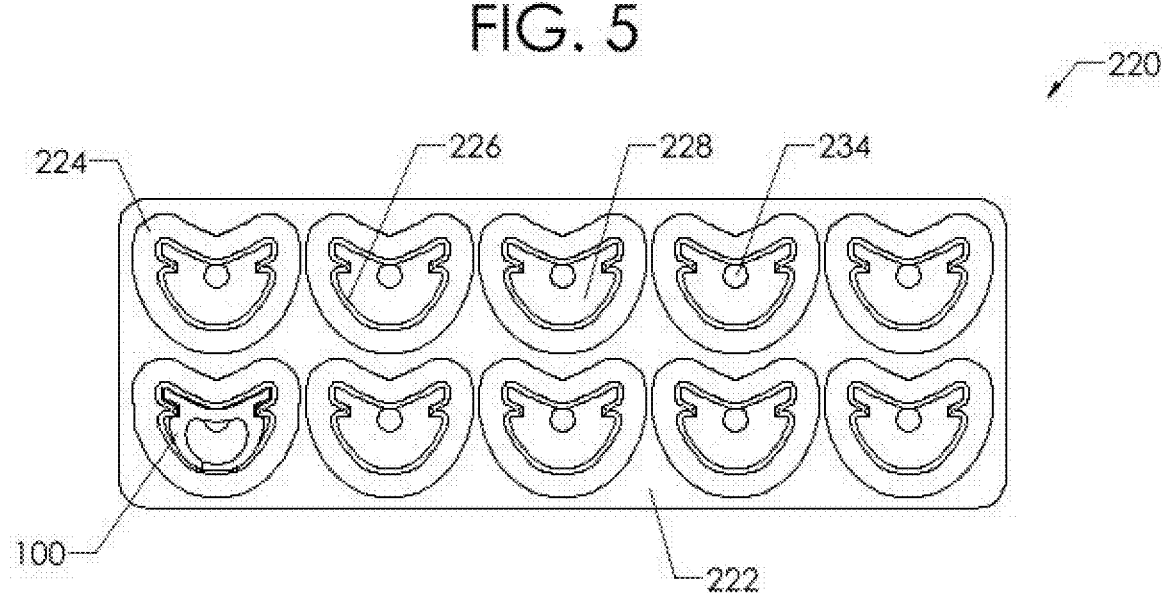
FIG. 5 is a top plan view of a second exemplary form for creating clips described herein.
Figure 6:
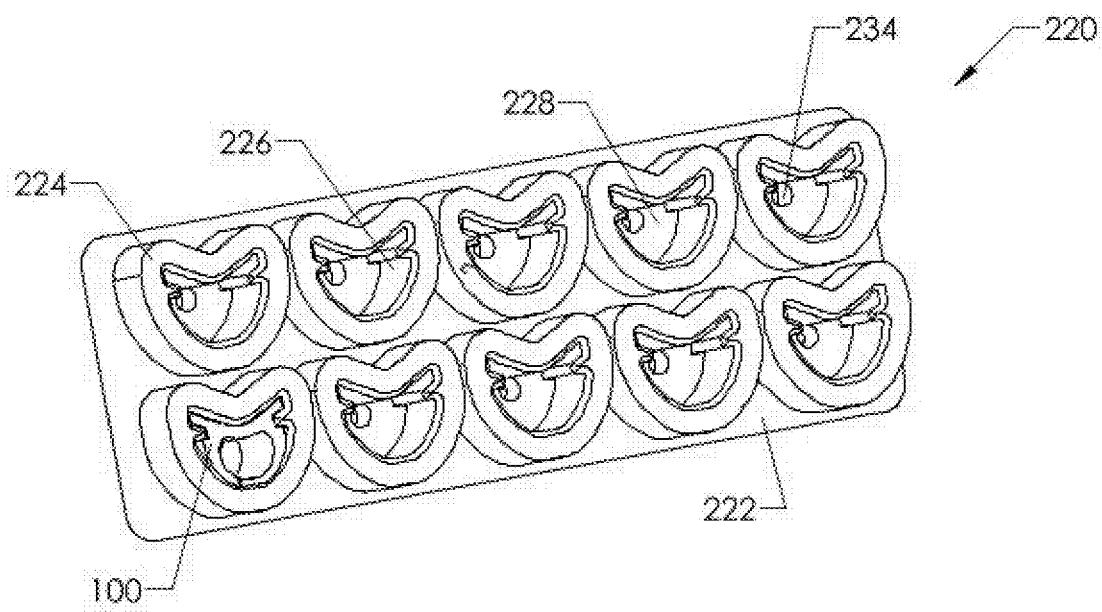
FIG. 6 is a top perspective view of the second exemplary form of FIG. 5.

FIGS. 5 and 6 show a second exemplary form 220 for use in manufacturing or creating clips (including clips 100). The shown second exemplary form 220 includes a field 222 with a plurality of clip form wells 224. Each clip form well 224 has an interior wall 226 that is preferably substantially coextensive with at least the majority of the exterior surface 101a of the clip 100 (e.g. the top portion 110 and the opposing sides 120 and 122 but not the faces 130 and 132). Each clip form well 224 also has a back surface 228 (that may be contiguous with the field 222) that is preferably substantially coextensive with at least the majority of one of the faces 130 and 132 of a clip 100 positioned in a clip form well 204. The back surface 228 may also have an aperture 234 that may be used to assist in the removal of the clip 100 from the clip form well 224. There is no protrusion in the second exemplary form 220.

Figure 7:
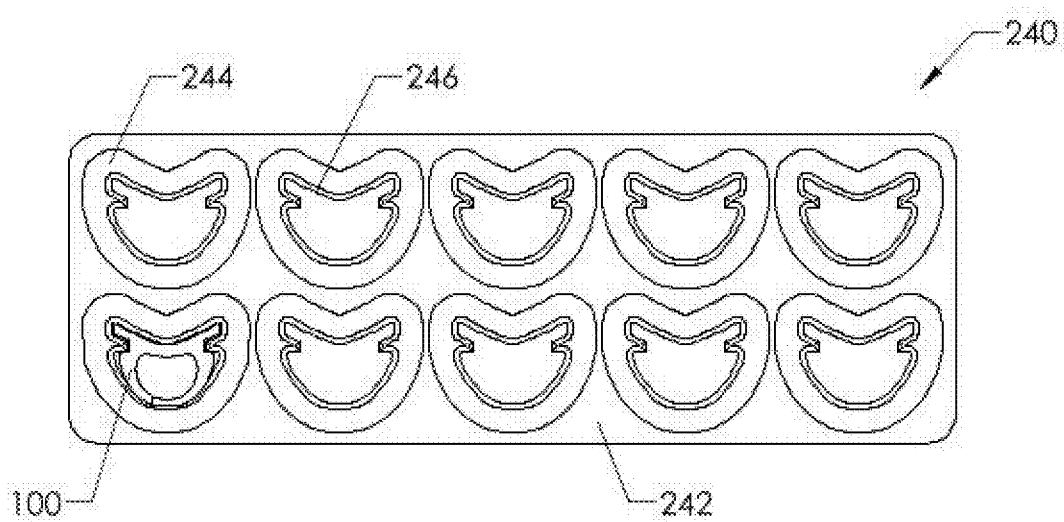
FIG. 7 is a top plan view of a third exemplary form for creating clips described herein.
Figure 8:
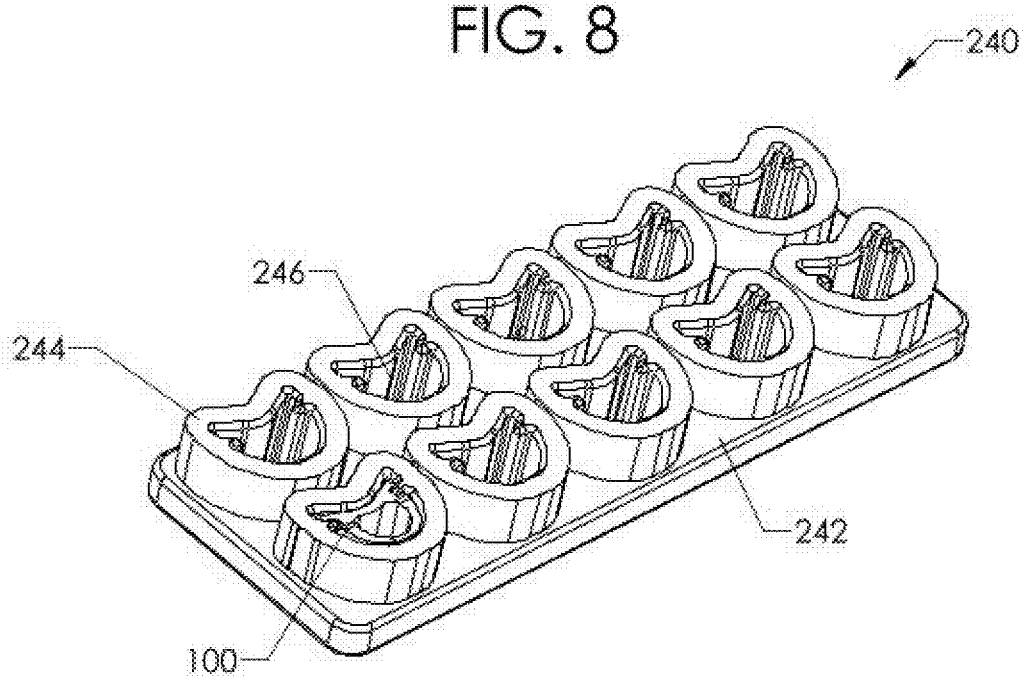
FIG. 8 is a top perspective view of the third exemplary form of FIG. 7.
Figure 9:
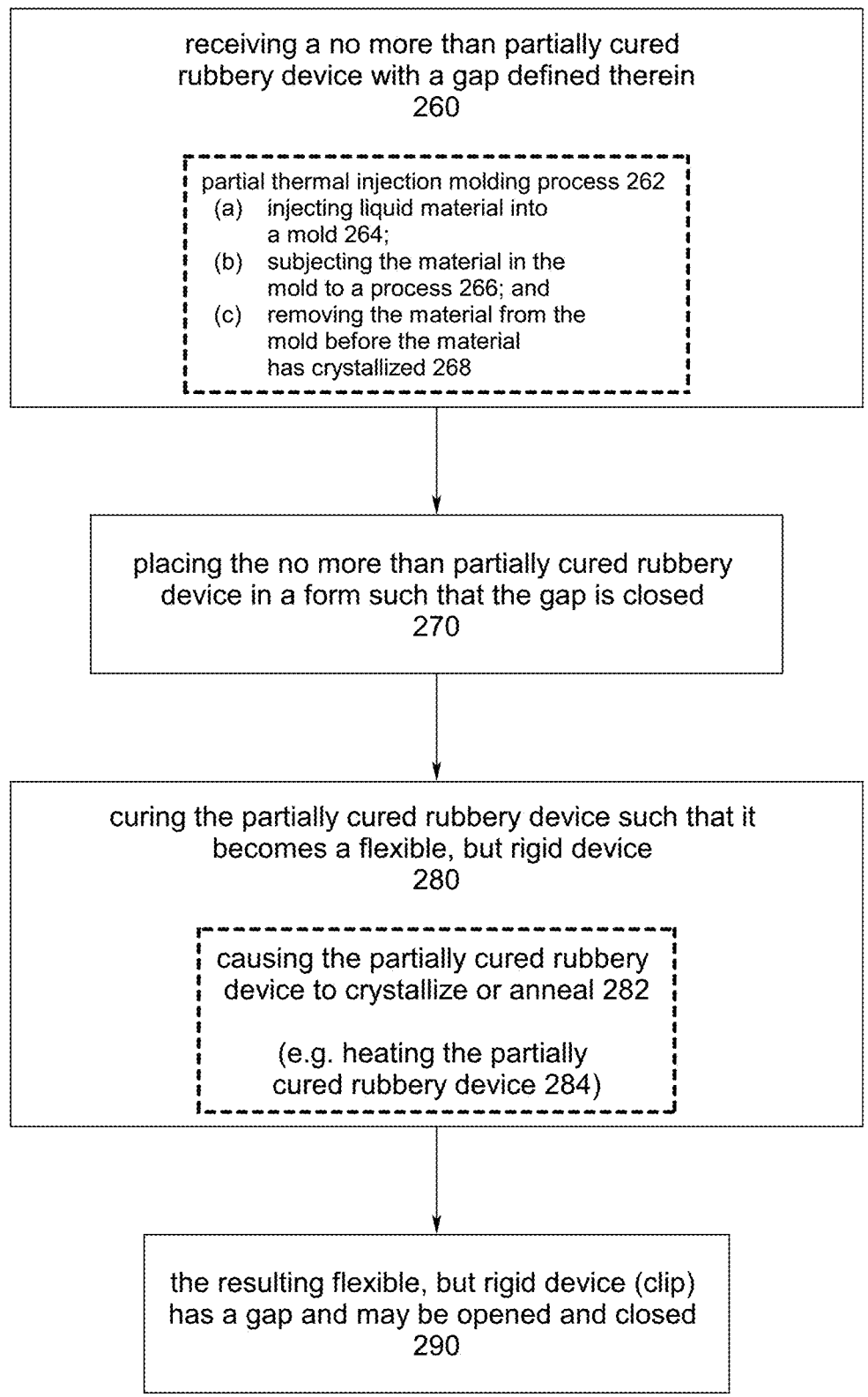
FIG. 9 is a flow chart showing steps in an exemplary process for using forms to create clips.

FIGS. 7 and 8 show a third exemplary form 240 for use in manufacturing or creating clips (including clips 100). The shown third exemplary form 240 includes a field 242 with a plurality of clip form wells 244. Each clip form well 244 has an interior wall 246 that is preferably substantially coextensive with at least the majority of the exterior surface 101a of the clip 100 (e.g. the top portion 110 and the opposing sides 120 and 122 but not the faces 130 and 132). There is no back surface or protrusion in the third exemplary form 240.

FIG. 9 shows an exemplary process for using the forms 200, 220, 240 to create clips 100. As shown in FIG. 9, an exemplary device forming process as described herein preferably includes the steps of: (1) receiving a no more than partially cured rubbery device with a gap defined therein 260; (2) placing the no more than partially cured rubbery device in a form such that the gap is closed 270 (touching gap); and (3) curing the partially cured rubbery device such that it becomes a flexible but rigid device 280. The step of receiving a partially cured rubbery device 260 may include the step of using a partial thermal injection molding process 262 to create a no more than partially cured rubbery device with a gap defined therein. The partial thermal injection molding process 262 may include the steps of: (a) injecting fluid clip material into a mold 264; (b) subjecting the clip material in the mold to a process 266; and (c) removing (ejecting) the clip material from the mold before the clip material has crystallized 268. The step of curing the partially cured rubbery device 280 may include the step of causing the partially cured rubbery device to crystallize or anneal 282. (It should be noted that the step of removing/ejecting 268 could, alternatively, be adjusting the mold by, for example, removing the wall or barrier of the mold and reducing the size of the mold or angling the sides thereof to remove the slight gap created by the wall or barrier.) The step of curing the partially cured rubbery device 280 may include, for example, the step of heating the partially cured rubbery device 284. The device forming process results in the formation of a flexible but rigid device (clip) that has a gap and may be opened (spread) and closed (narrowed to the point of the teeth touching) 290. The device should have shape memory as described herein. An open gap is a "spread gap" and a closed gap is a "touching gap."

Appliers

Figure 10:
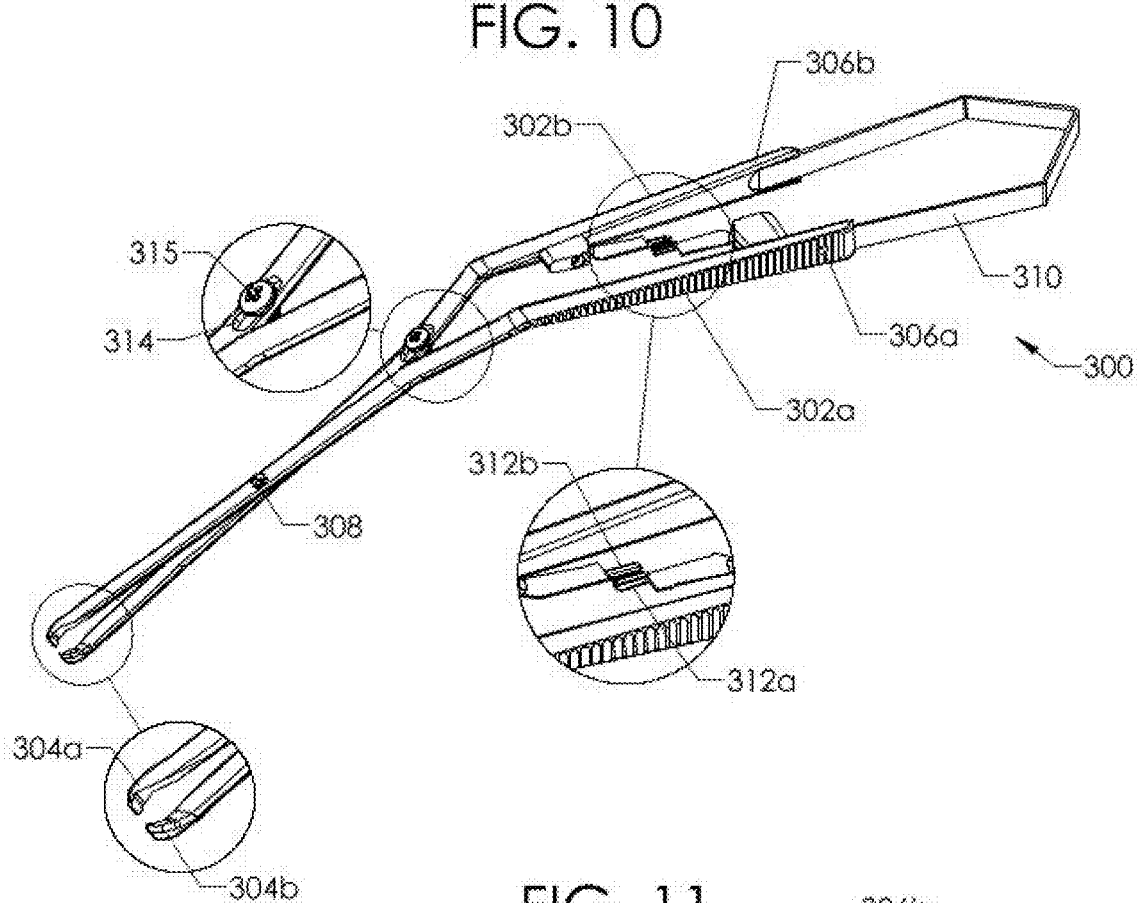
FIG. 10 is a perspective view of a first preferred applier in the un-pinched stage, the lock being unengaged (unlocked).
Figure 11:
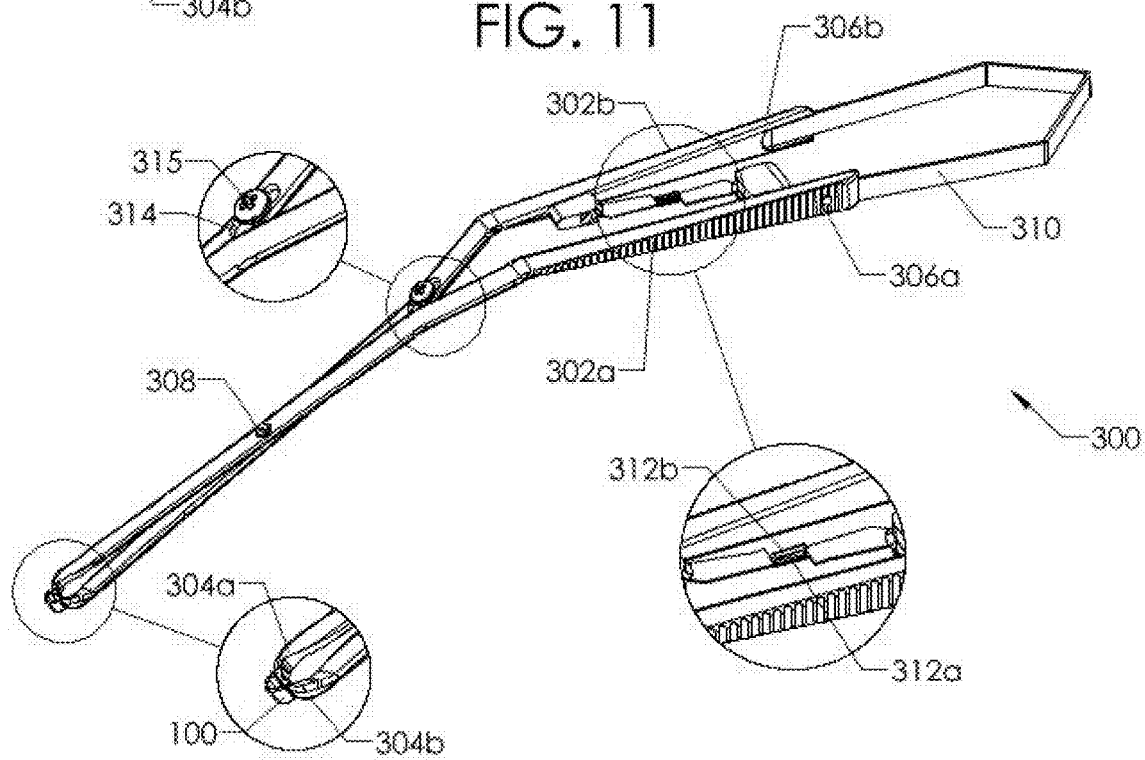
FIG. 11 is a perspective view of the first preferred applier in the partially-pinched stage, the lock being engaged (locked).
Figure 12:
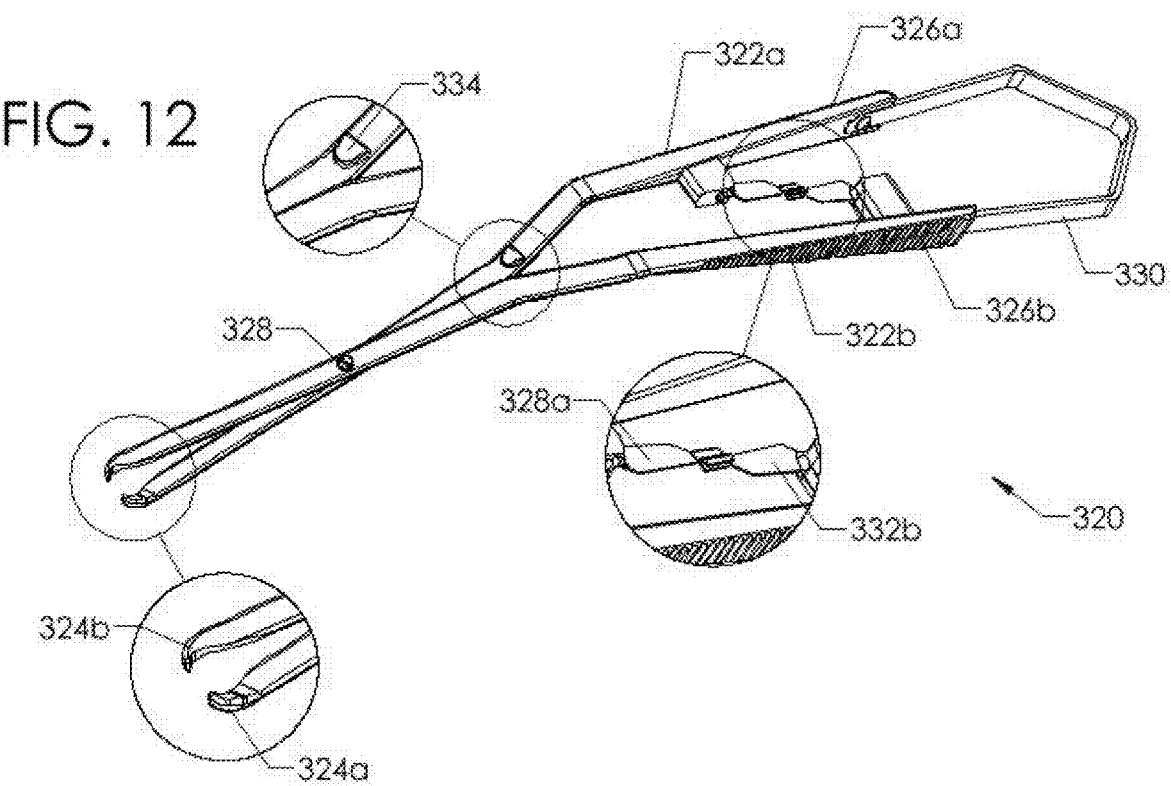
FIG. 12 is a perspective view of a second preferred applier in the un-pinched stage, the lock being unengaged (unlocked).
Figure 13:
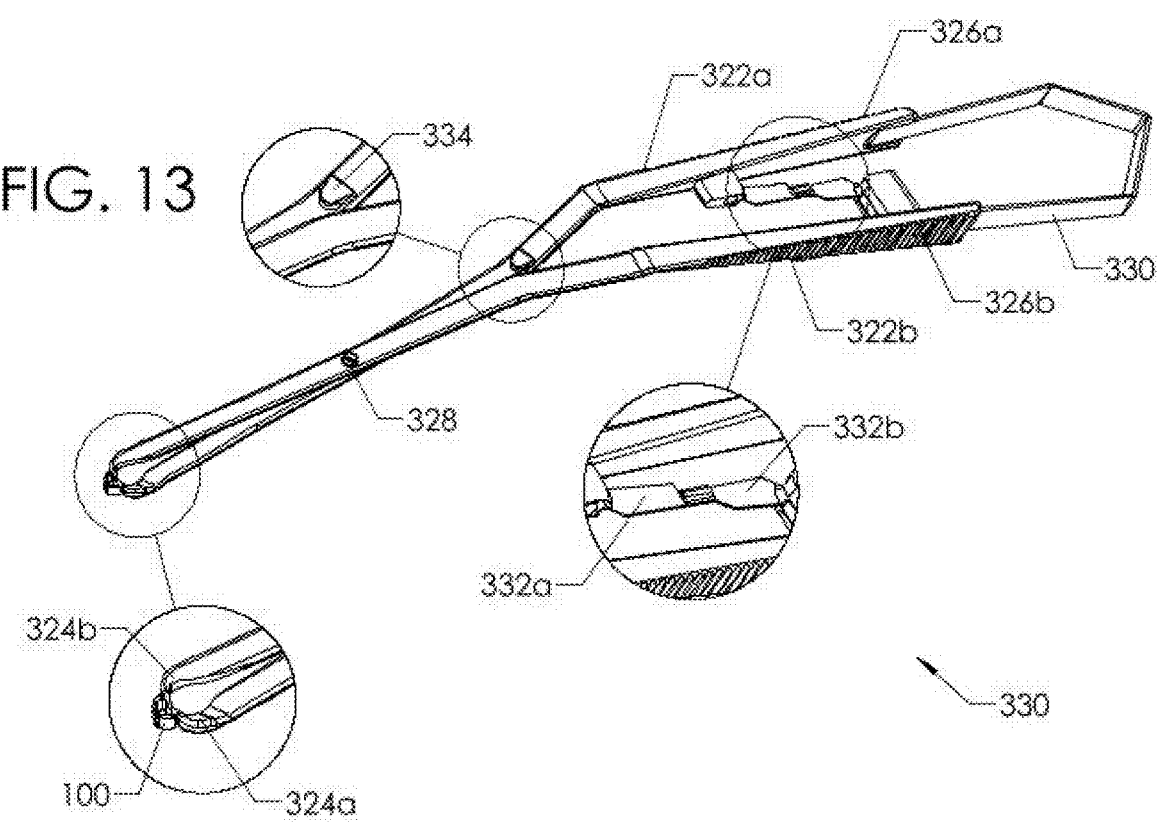
FIG. 13 is a perspective view of the second preferred applier in the partially-pinched stage, the lock being engaged (locked).
Figures 14, 15:
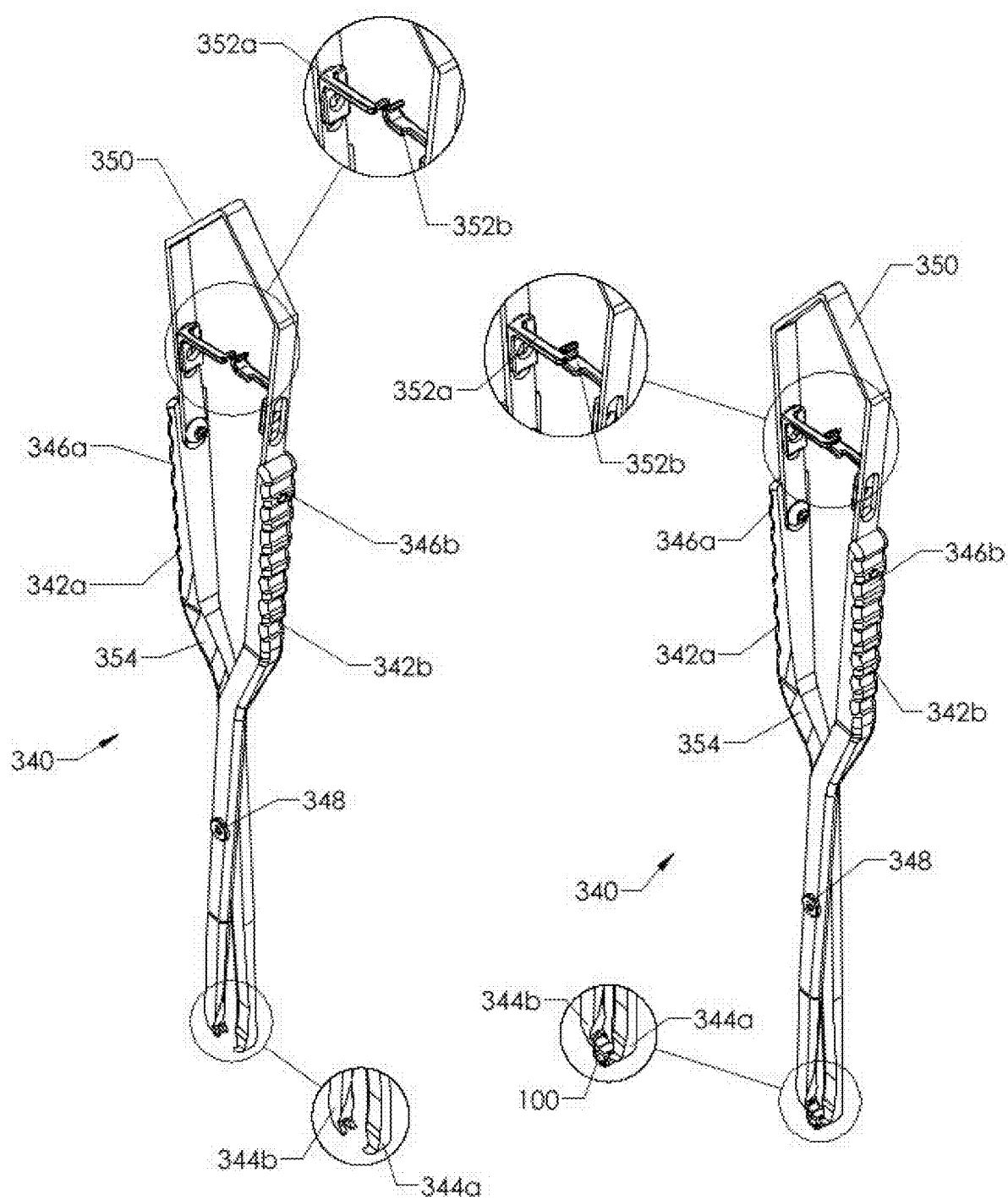
FIG. 14 is a perspective view of a third preferred applier in the un-pinched stage, the lock being unengaged (unlocked).
FIG. 15 is a perspective view of the third preferred applier in the partially-pinched stage, the lock being engaged (locked).
Figure 19:
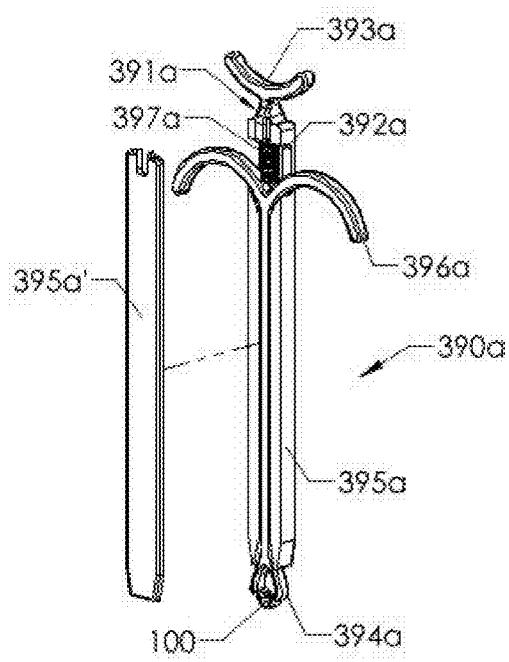
FIG. 19 is a perspective view of a fourth alternative applier that is a pusher-sleeve applier.
Figure 20:
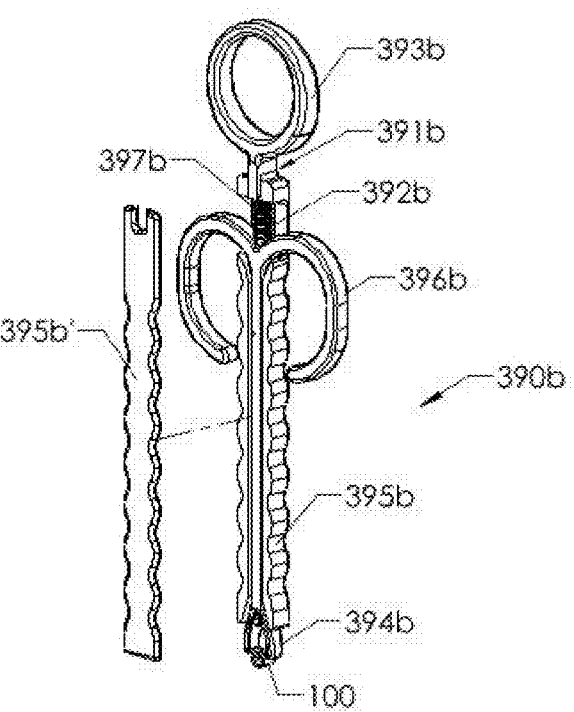
FIG. 20 is a perspective view of a fifth alternative applier that is a pusher-sleeve applier.

Three exemplary preferred appliers 300, 320, 340 are shown in FIGS. 10-15. More specifically, FIGS. 10-11 show a first preferred applier 300, FIGS. 12-13 show a second preferred applier 320, and FIGS. 14-15 show a third preferred applier 340. Additional appliers are shown in FIGS. 16-22.

In general, each of the shown exemplary preferred appliers 300, 320, 340 includes a pair of shafts 302a-b, 322a-b, 342a-b (also referred to as the first shaft and the second shaft). One end of each shaft (the first shaft tip end and the second shaft tip end) is a pinching tip 304a-b, 324a-b, 344a-b and the other end of each shaft (the first shaft handle end and the second shaft handle end) is a handle 306a-b, 326a-b, 346a-b. The pairs of shafts 302a-b, 322a-b, 342a-b are pivotally connected at a midpoint by a securing pivot 308, 328, 348 (e.g. a shoulder screw, rivet, bolt and nut combination, dowel pin, pin with retaining rings (e-clips), or a hinge pin). (As the shaft midpoints are covered by the securing pivot 308, 328, 348, the same reference numbers point to the shaft midpoints. The shaft midpoint is a point between the ends of the shafts, and not necessarily an exact middle.) Each of the shown exemplary preferred appliers 300, 320, 340 includes an optional exemplary lock 312a-b, 332a-b, 352a-b that can engage and disengage.

The appliers 300, 320, 340 have three basic stages: an un-pinched stage, a partially-pinched stage, and a pinched stage.

In the un-pinched stage (which can be thought of as the neutral or released stage) both the applier pinching tips 304a-b, 324a-b, 344a-b and the handles 306a-b, 326a-b, 346a-b are relatively far apart (the distance between the tips has been widened or increased). The distance 500 (FIG. 36) between the applier pinching tips 304a-b, 324a-b, 344a-b is sufficiently wide to pass over the clip wings 140 and 142. The lock 312a-b, 332a-b, 352a-b is unengaged (unlocked). The first figure (FIGS. 10, 12, and 14) of each set of figures for the exemplary preferred appliers 300, 320, 340 shows the appliers in the un-pinched stage. In the timeline series of figures (FIGS. 36-50), the applier is shown in the un-pinched stage in, for example, FIGS. 36, 48, and 49.

In the partially-pinched stage (which can be thought of as the removal or carrying stage), both the applier pinching tips 304*a-b*, 324*a-b*, 344*a-b* and the handles 306*a-b*, 326*a-b*, 346*a-b* are partially widened as a result of a "medium" amount of inward pressure (shown as single arrows in FIG. 40) being applied to the handles 306*a-b*, 326*a-b*, 346*a-b*. The distance 510 (FIG. 41) between the applier pinching tips 304*a-b*, 324*a-b*, 344*a-b* is sufficient to engage the clip grooves 150 and 152. The lock 312*a-b*, 332*a-b*, 352*a-b* is engaged (locked). The second figure (FIGS. 11, 13, and 15) of each set of figures for the exemplary preferred appliers 300, 320, 340 shows the appliers in the partially-pinched stage, the lock 312*a-b*, 332*a-b*, 352*a-b* being engaged (locked). In the timeline series of figures, the applier is shown in the partially-pinched stage in, for example, FIGS. 37-42.

In the pinched stage (which can be thought of as the clip opening stage), both the applier pinching tips 304*a-b*, 324*a-b*, 344*a-b* and the handles 306*a-b*, 326*a-b*, 346*a-b* are relatively close together (the distance 520 (FIG. 44) between the tips has been contracted or decreased) as a result of a "maximum" amount of inward pressure (shown as double arrows in FIG. 43) being applied to the handles. In the pinched stage, the pinching tips 304*a-b*, 324*a-b*, 344*a-b* apply pressure to the clip grooves 150 and 152 which, in turn, causes the sides 120 and 122 of the clip 100 to spread to the open position. The lock 312*a-b*, 332*a-b*, 352*a-b* is unengaged (unlocked). In the timeline series of figures, the applier is shown in the pinched stage in, for example, FIGS. 43-47.

The transitions between stages is described herein as being caused by different amounts of pressure (e.g. a "medium" amount of inward pressure and a "maximum" amount of inward pressure). The cause of the transition may be described in alternative terms and/or may actually be an alternative cause. For example, the transitions may be "caused" by "distance moved" in that moving the handles a "partial" distance causes the appliers 300, 320, 340 to transition from a first stage (e.g. the un-pinched stage) to a second stage (e.g. the partially-pinched stage), and moving the handles a "full" distance causes the appliers 300, 320, 340 to transition from the second stage (e.g. the partially-pinched stage) to a third stage (e.g. the pinched stage). Another example may be described in relation to the lock (depressing/squeezing the handles with a clip in the jaws causes the lock to engage so the clip is held securely in the "closed" position (the partially-pinched stage), then depressing/squeezing the handles again all the way to the stop causes the clip to open to it's maximum safe distance (the pinched stage)).

It should be noted that the appliers 300, 320, 340 may transition between the stages in intermediate stages that are not shown. Further, it is possible to "skip" a stage. For example, a user may start with an applier 300, 320, 340 in the un-pinched stage, pick up a clip 100 without formally engaging the lock (and, therefore, the applier 300, 320, 340 is not technically in the partially-pinched stage), and open the clip 100 by transitioning the applier 300, 320, 340 into the pinched stage. Releasing all pressure from the applier 300, 320, 340 in the pinched stage will cause the applier 300, 320, 340 to transition to the un-pinched stage.

As set forth above, each of the exemplary preferred appliers 300, 320, 340 includes a pair of shafts 302*a-b*, 322*a-b*, 342*a-b* (including a first shaft 302*a*, 322*a*, 342*a* and a second shaft 302*b*, 322*b*, 342*b*). One end of each shaft is an inwardly-angled pinching tip 304*a-b*, 324*a-b*, 344*a-b* and the other end of each shaft is a handle 306*a-b*, 326*a-b*, 346*a-b*. The pinching tips 304*a-b*, 324*a-b*, 344*a-b* may be notched or otherwise shaped to properly interact with the clips and/or the cartridges. The pairs of shafts 302*a-b*, 322*a-b*, 342*a-b* are pivotally connected at a midpoint (between the pinching tips 304*a-b*, 324*a-b*, 344*a-b* and the handles 306*a-b*, 326*a-b*, 346*a-b*) by a securing pivot 308, 328, 348. As shown, the shaft midpoints are not necessarily at the absolute middle of the shafts, but may be at many different locations between the pinching tips 304*a-b*, 324*a-b*, 344*a-b* and the handles 306*a-b*, 326*a-b*, 346*a-b*.

The handle ends 306*a-b*, 326*a-b*, 346*a-b* are shown as being attached by and pushed apart (or otherwise encouraged to increase their distance from each other) by an expander 310, 330, 350 (e.g. a spring expander such as a leaf spring or coil spring that encourages spreading). As shown, each end of the expander 310, 330, 350 is attached to one of the handle ends 306*a-b*, 326*a-b*, 346*a-b*. The ends of each expander 310, 330, 350 may be integral with the respective ends of the handles 306*a-b*, 326*a-b*, 346*a-b* so that the components are an integral shaft-expander-shaft unit. (FIG. 16 shows an alternative applier 360 in which the expander 362 is integral with the handles 364*a-b*.) Although shown at the end of the handles 306*a-b*, 326*a-b*, 346*a-b*, the respective expanders 310, 330, 350 may be in alternative locations. (FIG. 17 shows an alternative applier 370 in which the expander 372 is located about mid-way between the ends of the handles 374*a-b* and the securing pivot 376.)

Each of the shown exemplary preferred appliers 300, 320, 340 includes an optional lock 312*a-b*, 332*a-b*, 352*a-b* that can engage and disengage. When the lock is engaged, the appliers 300, 320, 340 are in the partially-pinched stage and the shafts 302*a-b*, 322*a-b*, 342*a-b* are essentially held together (preventing the distance between the handles 306*a-b*, 326*a-b*, 346*a-b* from widening) such that the pinching tips 304*a-b*, 324*a-b*, 344*a-b* engage the grooves 150 and 152 of the clip 100 (the partially-pinched stage) so that the clip 100 is held and can be carried by the appliers 300, 320, 340. When the lock 312*a-b*, 332*a-b*, 352*a-b* is engaged, the user does not need to continue to exert force on (pinch) the handles 306*a-b*, 326*a-b*, 346*a-b*. Disengaging the lock 312*a-b*, 332*a-b*, 352*a-b* allows the appliers 300, 320, 340 to either enter the un-pinched stage or the pinched stage. If, after the lock 312*a-b*, 332*a-b*, 352*a-b* is disengaged, no pressure is applied to the handles 306*a-b*, 326*a-b*, 346*a-b*, then the appliers 300, 320, 340 revert to the un-pinched stage because the expander 310, 330, 350 pushes the respective ends of the handles 306*a-b*, 326*a-b*, 346*a-b* outward (apart), which pivots (rotates) the securing pivot 308, 328, 348 such that the inwardly-angled pinching tips 304*a-b*, 324*a-b*, 344*a-b* also spread apart, releasing the clip 100. If, after the lock 312*a-b*, 332*a-b*, 352*a-b* is disengaged, additional pressure (shown as two arrows in FIG. 43) is applied to the handles 306*a-b*, 326*a-b*, 346*a-b*, then the appliers 300, 320, 340 enter the pinched stage because the pressure applied by the user pushes the respective ends of the handles 306*a-b*, 326*a-b*, 346*a-b* inward (together), which pivots (rotates) the securing pivot 308, 328, 348 such that the inwardly-angled pinching tips 304*a-b*, 324*a-b*, 344*a-b* also move toward each other, pinching the grooves 150 and 152 of the clip 100 and causing the sides 120 and 122 of the clip 100 to spread to the open position.

Preferred locks 312a-b, 332a-b, 352a-b each have two parts, a first lock part 312a, 332a, 352a associated with a first shaft 302a, 322a, 342a, and a second lock part 312b, 332b, 352b associated with a second shaft 302b, 322b, 342b. (It should be noted that the lock 352a-b of FIGS. 14-15 is different from the locks 312a-b, 332a-b of FIGS. 10-11 and FIGS. 12-13. Other designs are possible.) The shown locks 312a-b, 332a-b, 352a-b each have two parts, a first lock part 312a, 332a, 352a associated with a first handle 306a, 326a, 346a, and a second lock part 312b, 332b, 352b associated with a second handle 306b, 326b, 346b. Each first lock part 312a, 332a, 352a interacts with its associated second lock part 312b, 332b, 352b to engage (lock) and disengage (unlock). When the locks 312a-b, 332a-b, 352a-b are engaged, the handles 306a-b, 326a-b, 346a-b are substantially held together (generally preventing the distance between the handles 306a-b, 326a-b, 346a-b from widening, although some movement may be possible, particularly if it is necessary to move the handles 306a-b, 326a-b, 346a-b to disengage the locks 312a-b, 332a-b, 352a-b). When the parts of the locks 312a-b, 332a-b, 352a-b are disengaged, the handles 306a-b, 326a-b, 346a-b are able to move toward or away from each other. The shown first lock parts 312a, 332a, 352a have a "hook" extending from the first handle 306a, 326a, 346a generally in the direction of the second handle 306b, 326b, 346b. The shown second lock parts 312b, 332b, 352b have a "hook" extending from the second handle 306b, 326b, 346b generally in the direction of the first handle 306a, 326a, 346a. (Similar hooks can be found in U.S. Pat. No. 2,652,832 to Castroviejo. The "hooks" are located so that when the handles 306a-b, 326a-b, 346a-b are moved toward each other (and perhaps in a slight off-planar movement), the hooks can engage. The handles 306a-b, 326a-b, 346a-b can be moved toward each other (and perhaps in a slight off-planar movement) to disengage the hooks.

Although shown on the inner surfaces of the handles 306a-b, 326a-b, 346a-b, the respective parts of the locks 312a-b, 332a-b, 352a-b may be in alternative locations. For example, the parts of the locks 312a-b, 332a-b, 352a-b may be located (including adjustably located) on the ends of the expanders 310, 330, 350 near the handles 306a-b, 326a-b, 346a-b. Another example is that the parts of the locks 312a-b, 332a-b, 352a-b may be located and held in place using the same location fixers (e.g. bolts and nuts) that join the ends of the expanders 310, 330, 350 to the ends of the handles 306a-b, 326a-b, 346a-b.

Although shown as hooks, other locks could be used including, but not limited to, magnets, or other locking mechanisms known or yet to be discovered. Although the shown locks 312a-b, 332a-b, 352a-b have two relatively similar interacting parts (e.g. two hooks), alternative locks could have unequal parts. For example, one part of the lock could be a hook on one shaft and the other part of the lock could be a loop associated with the other shaft. In yet another alternative lock, one part of the lock could be a hook on one shaft and the other part of the lock could be a part of the opposite shaft itself.

Each of the shown exemplary preferred appliers 300, 320, 340 also includes at least one optional limiter 314, 315, 334, 354. The purpose of the optional limiter 314, 315, 334, 354 is to prevent the pinching tips 304a-b, 324a-b, 344a-b from damaging a clip 100 (over-opening or otherwise experiencing plastic deformation) by squeezing it too hard in the pinched stage. The shown exemplary optional limiter may be an adjustable limiters 314, 315 (shown in FIGS. 10-11 as a slot 314 with a location fixer 315 (e.g. bolts and nuts)) or a built-in limiter 334, 354 (e.g. shown in FIGS. 12-13 a bump or protrusion 334 (protrusion limiter) and shown in FIGS. 14-15 a shoulder 354 (shoulder limiter)). The limiter 314, 315, 334, 354 may be associated with the first handle 306a, 326a, 346a and/or the second handle 306b, 326b, 346b. Alternatively, the limiter could be located near the pinching tips 304a-b, 324a-b, 344a-b. When the handles 306a-b, 326a-b, 346a-b are squeezed together during the pinched stage, the optional limiter 314, 315, 334, 354 prevents the handles 306a-b, 326a-b, 346a-b (and thereby the pinching tips 304a-b, 324a-b, 344a-b) from getting closer than a predetermined distance apart and over-opening the clip.

While the exemplary preferred appliers 300, 320, 340 are similar to each other as is shown from the figures and the above discussion, there are some differences. For example, both the first applier 300 and the second applier 320 are angled (shown as the shafts 302a-b, 322a-b having a bend at an approximately 30 degree angle between the lock 312a-b, 332a-b and the limiter 314, 334), whereas the third applier 340 is "straight" or "unbent" (the shafts 342a-b are straight). The bend in the angled/bent appliers may help to increase visibility during use by displacing the user's hand from the user's line of sight. Alternative bent versions could have the bend at a different location (e.g. more toward the tip) or multiple bends (e.g. a "bayonet handle"). Other differences are proportions. For example, the handles 306a-b, 326a-b of the first and second appliers 300, 320 are longer than the handles 346a-b of the third applier 340. Another example is that the pinching tips 304a-b, 324a-b of the first and second appliers 300, 320 do not have a notch, whereas the pinching tips 344a-b of the third applier 340 do have a notch. Yet another example is that the first applier 300 is shown with an adjustable limiter 314, 315, whereas the second and third appliers 320, 340 are shown with built-in limiters 334, 354. Still another example is that the built-in limiter shown in FIGS. 12-13 is a bump or protrusion 334 (protrusion limiter), whereas the built-in limiter shown in FIGS. 14-15 is a shoulder limiter 354 (and, more specifically, a ramp shoulder limiter in which the ramp portion gets gradually thicker to eventually prevent limit how close the handles can come to each other). Yet other differences (e.g. the presence or absence of components and/or the location of components) will be shown and discussed in relation to the appliers shown in FIGS. 16-22.

FIG. 16 shows an alternative applier 360 in which the expander 362 is integral with the handles 364a-b. As shown, the components are an integral shaft-expander-shaft unit. This applier 360 has a pivot 366 that is relatively close to the tips 367a, 367b. This applier 360 also has at least one shoulder limiter 369 (it may have a shoulder limiter on both faces). This shoulder limiter 369 is shown as being more abrupt than the ramp shoulder limiter 354 of FIGS. 14-15. The applier 360 of FIG. 16 is an example of an applier without a lock.

FIG. 17 shows an alternative applier 370 in which the expander 372 is located about mid-way between the ends of the handles 374a-b and the pivot 376. The pivot 376 that is relatively close to the tips 377a, 377b. The shown expander 372 is a compression spring that is shown as being attached to protrusions on the inside of the handles 374a-b. This applier 370 also has a shoulder limiter 379. This shoulder limiter 379 is shown as being more abrupt than the ramp shoulder limiter 354 of FIGS. 14-15. The applier 370 of FIG. 17 is another example of an applier without a lock.

FIG. 18 shows an alternative applier 380 that works on a different principle than others described herein. The applier 380 includes two "shafts" 281a-b each having a handle 382a-b at one end and a pinching tip 384a-b at the other. The shafts 281a-b are curved or bent (including a bent central shaft portions 383a-b) as shown in FIG. 18 such that when they overlap, the handles 382a-b are at one end and the pinching tips 384a-b are at the other end, and there is a central opening 383 (defined between the central shaft portions 383a-b) between the two ends. As shown, on each face of each bent central shaft portion 383a-b there is a protrusion 385a, 385b to which springs 386 (there may be one on each face, although only one spring 386 is clearly shown in the figure) are attached so the springs span the central opening 383. The central opening 383 is located between two overlapping sections 387a, 387b. At least one of the overlapping sections 387a, 387b has a securing pivot 388. This applier 380 also has two shoulder limiters 389, one on each face of the applier 380. These shoulder limiters 379 are shown as being more abrupt than the ramp shoulder limiter 354 of FIGS. 14-15. When the handles 382a-b of this applier 380 are squeezed together, the pinching tips 384a-b separate (the distance therebetween widens). Put another way, when the handles are depressed, the jaws (pinching tips 384a-b) open. When the pinching tips 384a-b are positioned over the clip 100, the pressure on the handles 382a-b is released and the force of the spring(s) 386 close(s) the pinching tips 384a-b. The springs 386 are chosen so that the applier 380 opens the clip 100 to a predetermined distance (the open position). This design allows the clip 100 to be held in the open position until the surgeon squeezes the handles 382a-b (causing the distance between the pinching tips 384a-b widens) to release the clip 100. Put another way, when the handles 382a-b are depressed again, the jaws (pinching tips 384a-b) open and the clip 100 is released. The surgeon would release the clip 100 when it was positioned to secure the everted ends of the tissue 600. Once released, the clip 100 would return to the closed position to hold the everted ends of the tissue 600 together.

Figure 21:
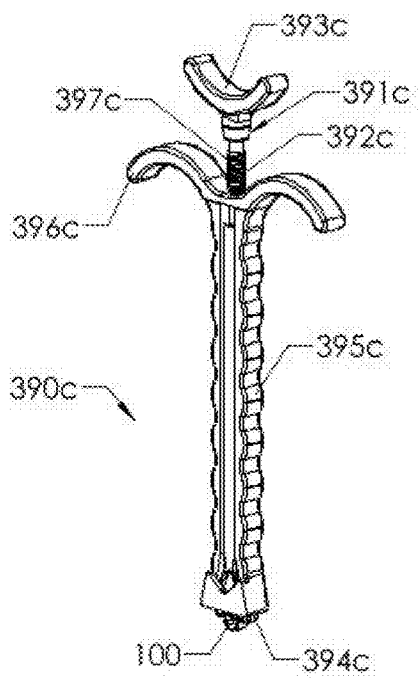
FIG. 21 is a perspective view of a sixth alternative applier that is a pusher-sleeve applier.
Figure 22:
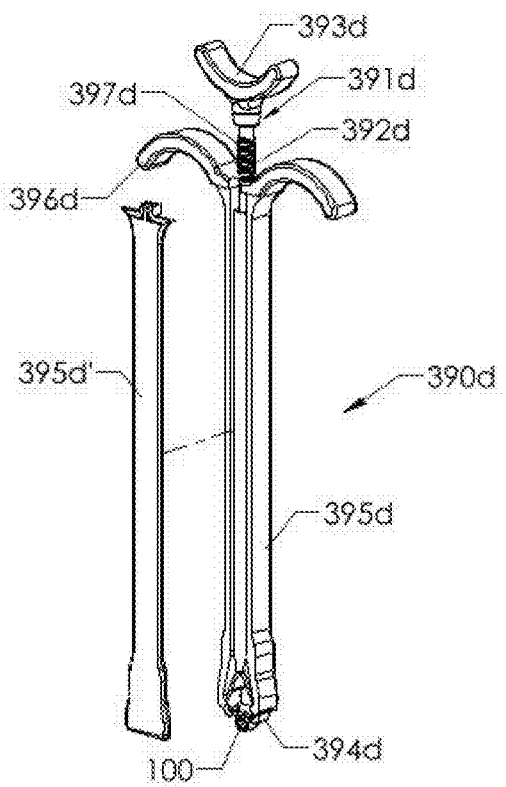
FIG. 22 is a perspective view of a seventh alternative applier that is a pusher-sleeve applier.

FIGS. 19-22 show alternative pusher-sleeve appliers 390a-d that also work on different principles than others described herein. These appliers 390a-d each have a pusher 391a-d with a pusher shaft 392a-d. At one end of the pusher shaft 392a-d is a pusher finger/thumb rest 393a-d and at the other end of the pusher shaft 392a-d is a pinching tip 394a-d (that includes two inwardly-turned tips that are outwardly-biased so that the inwardly-turned tips tend to spread apart when unconstrained). The pusher 391a-d is substantially surrounded by a sleeve 395a-d. (The covers 395a', 395b', 395d' are shown exploded from the body of the sleeves 395a, 395b, 395d to show the internal components. The sleeve 395c of FIG. 21 is designed without a cover. When referred to herein as the sleeve 395a-d, the cover is meant to be included unless it is specifically excluded.) At least one sleeve finger/thumb rest 396a-d is associated with each sleeve 395a-d. Upward pressure mechanism 397a-d (e.g. a spring) is installed between the pusher 391a-d and the sleeve 395a-d. The shown upward pressure mechanism 397a-d surrounds the pusher shaft 392a-d near the pusher finger/thumb rest 393a-d. The upward pressure mechanism 397a-d provides an upward bias so that the pusher 391a-d is pushed upward and the pinching tips 394a-d are drawn into the sleeve 395a-d. In use, depressing the pusher 391a-d causes the pinching tips 394a-d to extend out of the sleeve 395a-d. Since they are outwardly biased, the pinching tips 394a-d spread apart allowing the pinching tips 394a-d to pass the wings 140 and 142 of the clip 100. When the pressure on the pusher 391a-d is released, the upward pressure mechanism 397a-d provides an upward pressure that causes the pinching tips 394a-d to be drawn into the sleeve 395a-d, which moves the pinching tips 394a-d together to pinch the grooves 150 and 152 of the clip 100. Pinching the grooves 150 and 152 causes the sides 120 and 122 of the clip 100 to spread to the open position. As long as the pusher 391a-d is not depressed, the pinching tips 394a-d continue to hold the clip 100 in the open position. Depressing the pusher 391a-d again causes the pinching tips 394a-d to extend out of the sleeve 395a-d and spread apart, allowing the release of the clip 100 that reverts to the closed position.

Although the various applier components (e.g. the handles 306a-b, 326a-b, 346a-b, the expander 310, 330, 350, the lock 312a-b, 332a-b, 352a-b, and/or the limiter 314, 315, 334, 354) are shown in a fixed location, the locations of the components could be adjustable in relation to each other. Mechanical adjusting mechanisms such as slots and location fixers (e.g. bolts and nuts) may be used to allow adjustment between applier components. For example, slots could be added to the handles 306a-b, 326a-b, 346a-b to allow adjustment of the expander 310, 330, 350 (or the lock 312a-b, 332a-b, 352a-b or the limiter 314, 315, 334, 354) which are then held in place by a location fixer.

The appliers 300, 320, 340, 360, 370, 380, 390 may be single use or reusable. They are preferably made from medical grade applier materials including metals (e.g. stainless steel, titanium, aluminum), plastics (e.g. acrylic, polycarbonate, polypropylene, nylon, polyether ether ketone (PEEK), polysulfone) and/or other materials suitable for use in medical applications. One factor that may be taken into consideration when determining the specific applier material(s) to be used is whether the appliers are being designed for multiple uses (reusable) or only single use (disposable). If the applier is a reusable applier, the applier material would have to be re-sterilizable and strong enough to withstand multiple uses.

Cartridges

The forms 200, 220, 240, as described herein in relation to FIGS. 3-8, are the basis for the cartridges 400, 405, 410, 418, 420, 440, 450, 460, 470, 480 as they preferably can hold and form the clips 100 in the closed position for curing (crystallization and annealing). Further, the cartridges 400, 405, 410, 418, 420, 440, 450, 460, 470, 480 may hold and protect the clips 100 and otherwise function as packaging. (The cartridges 400, 405, 410, 418, 420, 440, 450, 460, 470, 480 may be designed to hold any number of clips 100, but most likely would hold between two (2) and ten (10) clips. The preferred shown cartridges hold five (5) clips.) Still further, the cartridges 400, 405, 410, 418, 420, 440, 450, 460, 470, 480 can be used to hold the clips 100 during a sterilization process (e.g. e-beam sterilization). Finally, the cartridges 400, 405, 410, 418, 420, 440, 450, 460, 470, 480 can be used to dispense the clips 100 during surgery using an applier (shown in some figures as applier 300 (FIG. 31) or applier 320 (FIGS. 33-34), although alternatives applier described herein could be used) to remove the clips 100.

While all the cartridges 400, 405, 410, 418, 420, 440, 450, 460, 470, 480 include a body 400', 405', 410', 418', 420', 440', 450', 460', 470', 480' with at least one formation well 401, 407, 411, 421, 441, 451, 461, 471, 481 defined therein, each of the cartridges 400, 405, 410, 418, 420, 440, 450, 460, 470, 480 shown in FIGS. 23-35 include their own respective array of features. The shown cartridges are exemplary preferred variations, but some of the features that are shown with respect to one exemplary cartridge can be used with exemplary cartridges other than those with which they are associated. Exemplary features include, but are not limited to, the following features:

a single elongated channel formation well into which a plurality of clips can be slideably loaded and removed horizontally (by sliding the clip along the length of the channel formation well);

a plurality of individual formation wells (pockets or cups) separated by dividers such that each of a plurality of clips has its own formation well (pocket);

formation structure such as formation pins or formation fingers;

guide and/or access structure (referred to generally as "guide structure") that provide(s) guidance and/or better access (referred to generally as "guidance") to assist the appliers in removing the clips from the formation wells;

blocking structure that blocks at least one side of a formation well;

gripping structure such as a handle, indented grips, and/or finger holder;

stabilizing structure (e.g. a stabilizer or foot) to help hold the cartridge upright for use; and clip securing structure (securers) that provide an additional mechanism to retain and secure the clips within the formation well(s).

As set forth, all the cartridges include at least one formation well. Preferred formation wells may be either a single elongated channel formation well or a plurality of formation wells (pockets). The formation wells (which may include additional formation structure) are designed to hold at least one clip 100 in the closed position with the teeth 120a and 122a preferably touching.

The formation wells described herein are distinctly different from clip storing chambers in known cartridges. For example, U.S. Patent Application Publication No. 2009/0152147 to Cannady is representative of known hemostatic clip cartridges in which clips straddle barriers (pedestals or walls) that prevent the open ends of the clips from touching while they are stored in the cartridge. Similarly, U.S. Pat. No. 4,146,130 to Samuels shows central binding posts that are positioned between the ends of the clips, the central binding post preventing the open ends of the clips from touching while they are stored in the cartridge. U.S. Pat. No. 4,519,501 to Cerwin shows representative clip cartridges in which the clips are held in an open position.

As discussed, the formation wells described herein are specifically designed to hold the clips 100 in the closed position with the teeth 120a and 122a preferably touching so that the "partially cured rubbery device" can finish curing. Holding the clips 100 in the closed position is accomplished by making the formation wells (or additional formation structure within the formation wells) in a size and/or shape that gently holds the sides 120 and 122 of the clip 100 close enough together so that the teeth 120a and 122a touch. Put another way, the surfaces of the formation wells (including the walls and/or floors of the formation wells) are designed (e.g. sized and/or shaped) so that the sides of the "partially cured rubbery device" have to bend toward each other (and are held in that position) so that the teeth 120a and 122a touch. The formation wells also preferably minimize clip movement when the clips are seated in the formation wells.

Figure 26A:
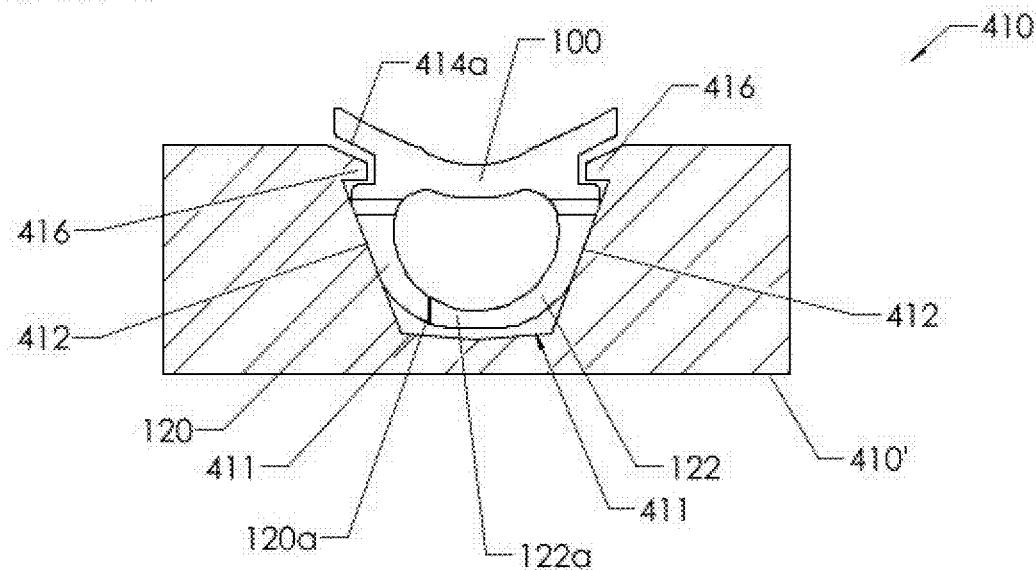
FIG. 26A is a cross-sectional view of a cartridge with a cartridge formation well with angled well surfaces and an overhang.

Cartridge 400 of FIGS. 23-24 is an exemplary cartridge with an exemplary single elongated channel formation well 401 with an optional overhang 401'. The single elongated channel formation well 401 is shown as having a generally rounded well surface 402 in cross-section. (A cross-section of an alternative exemplary elongated channel formation well 411 might have more angular well surfaces 412 as shown in FIG. 26A.) As shown, the well surfaces 402 (and the optional overhang 401') of the formation well 401 hold the sides 120 and 122 of the clips 100 in the closed position with the teeth 120a and 122a touching. Clips can be loaded and/or removed from the single elongated channel formation well horizontally (by sliding the clip(s) 100 along the length of the channel formation well and coming out at an end). Depending on the rigidness of the clips and/or the cartridge, clips can also, or in the alternative, be loaded and/or removed from the single elongated channel formation well vertically (pulling the clip upward from the channel formation well).

FIGS. 27-35 show cartridges 420, 440, 450, 460, 470, 480 with a plurality of formation wells 421, 441, 451, 461, 471, 481 separated by dividers 423, 443, 453, 463, 473, 483. While the cross-sections and/or surfaces (e.g. well surface 422) of the formation wells may be similar to those shown in FIGS. 23-25 (rounded) and FIG. 26A (angular), the formation wells may also, or in the alternative, include additional formation structure (e.g. formation pins 452 (FIGS. 30-31) or formation fingers 462 (FIGS. 32-33), 482 (FIG. 35)) to help form the clips and/or hold the clips in the closed position for curing. The well surfaces of the formation wells and/or the formation structure hold the sides 120 and 122 of the clips 100 in the closed position with the teeth 120a and 122a preferably touching.

Depending on the cartridges and formation wells, the clips 100 can be loaded and/or removed from the plurality of formation wells horizontally and/or vertically. For example, the configuration of the enclosed individual formation wells 421 of the cartridge 420 of FIGS. 27-28 would necessitate vertical removal (pulling the clip 100 upward from the channel formation well) and loading because the dividers 423 on either side of the formation wells 421 would prevent horizontal removal of the clips 100. On the other hand, the individual formation wells 451, 461 of the cartridges 450, 460 of FIGS. 30-31 and FIGS. 32-33 could optionally allow vertical removal (pulling the clip 100 upward from the individual formation wells, with the formation pins 452 or fingers 462 either bending out of the way or breaking off) and/or horizontal removal (sliding the clip 100 out through the open end of the individual formation wells) and loading (sliding the clip 100 in through the open end of the individual formation wells).

The shown cartridges 400, 405, 410, 418, 420, 440, 450, 460, 470, 480 preferably include at least some form of guide and/or access structure that provide(s) guidance and/or better access to assist in the appliers removing the clips from the formation wells 401, 407, 411, 421, 441, 451, 461, 471, 481. This guide and/or access structure may take forms such as angled surfaces 404a, 414a, 424a, 444a, 454a, 464a, side channels 404b, wall guides (raised borders or dividers) 424b, 444b, 454b, 464b, and/or other structure (particularly mechanical structure). (These and other guide and/or access structure are shown in other figures, although not specifically labeled as guide and/or access structure.) The guides and/or access structures may be used individually or in combination.

The cartridges may include one or more blocking structures that block at least one side of a formation well. These blocking structures block their respective formation wells and prevent clips from sliding out of the blocked ends of the formation wells. Further, these blocking structures may help in both loading and unloading clips from the formation wells. FIG. 25, for example, shows a cartridge 405 with an exemplary blocking structure 406 at one end of a single elongated channel formation well 407. As shown, side channels 408 may also be blocked at one end. Other examples include the blocking structure 455, 465, 485 at one end of the formation wells 451, 461, 481 in FIGS. 30-34. Technically, the dividers 423 (FIGS. 27-28) and 443 (FIG. 29) also act as blocking structures in that they block the clips from sliding out of either side of the formation wells of their respective cartridges.

Figure 30:
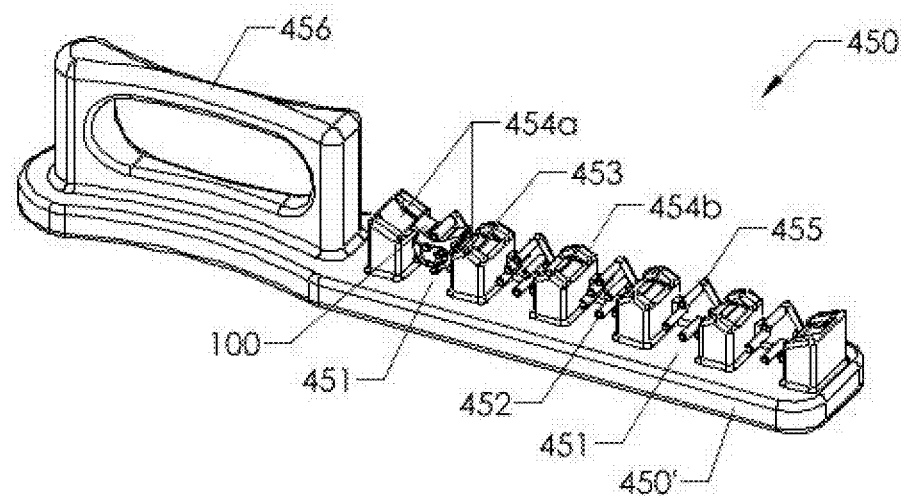
FIG. 30 is a perspective view of an exemplary cartridge with a plurality of formation wells that include formation pins, the cartridge having gripping structure inline with the cartridge body.
Figure 32:
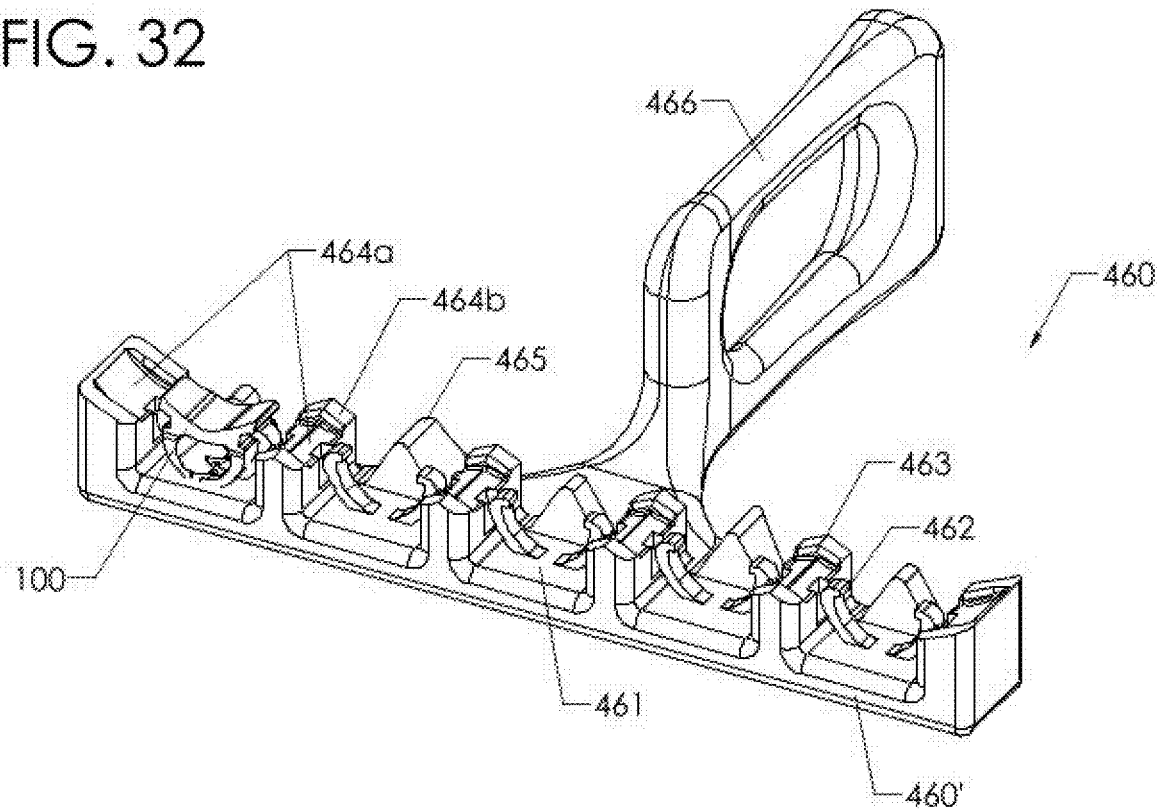
FIG. 32 is a perspective view of an exemplary cartridge with a plurality of formation wells that include formation fingers, the cartridge having gripping structure perpendicular to the formation wells such that the gripping structure functions as a stabilizer.
Figure 34:
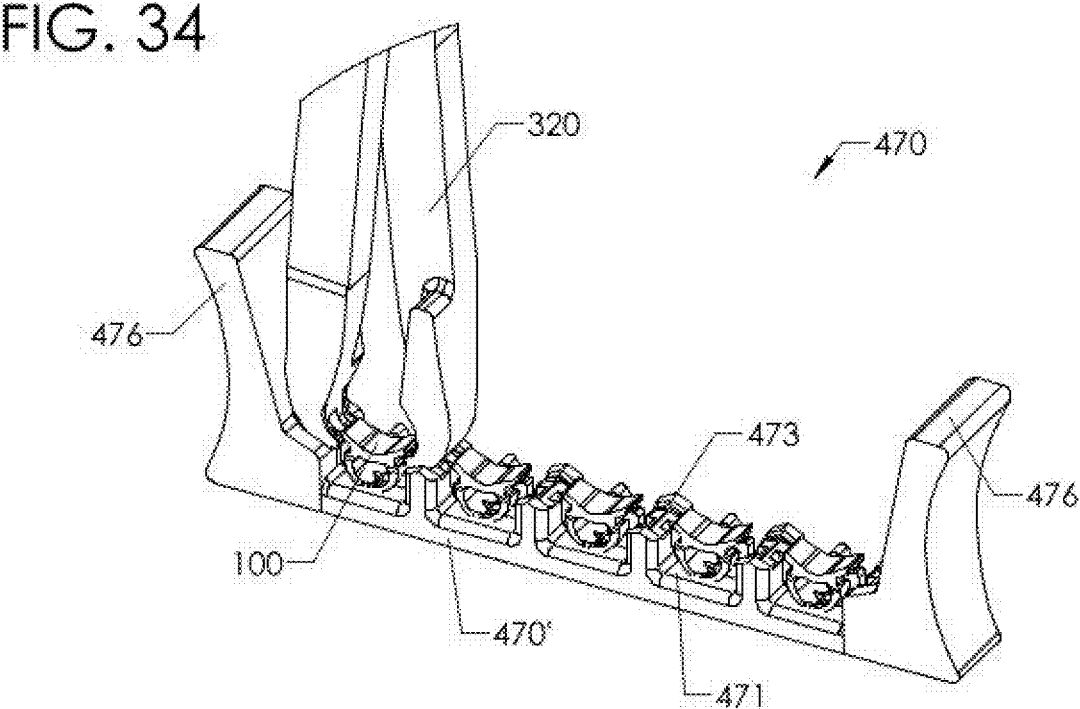
FIG. 34 is a side view of an exemplary cartridge with gripping structure at both ends, the cartridge having a plurality of formation wells, each of the formation wells shown with a clip therein, and an applier beginning to remove one clip.
Figure 35:
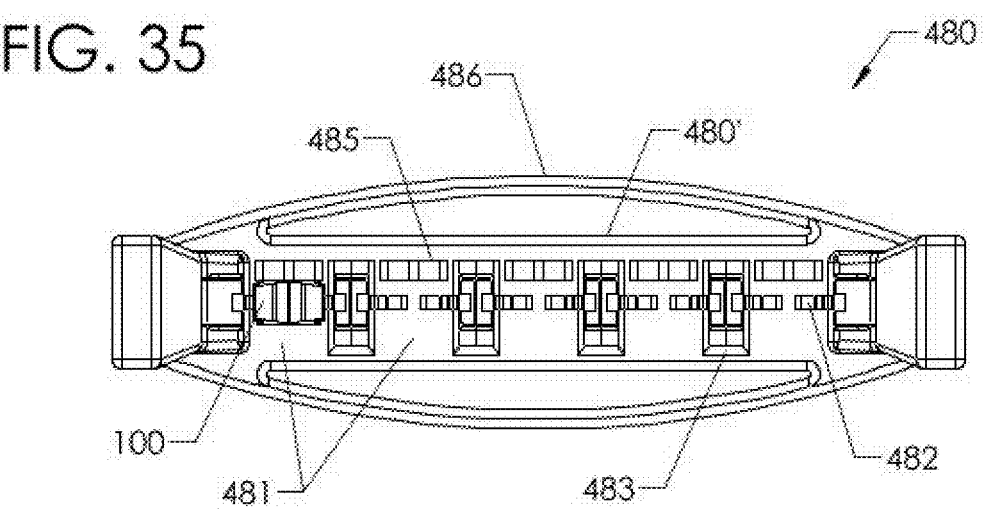
FIG. 35 is a top view of an exemplary cartridge with gripping structure at both ends and arced stabilizers on both sides of the body of the cartridge.

While the edges of the body 400', 405', 410', 418', 420', 440', 450', 460', 470', 480' of the respective cartridges may function as a gripping structure, additional gripping structure may also be provided. For example, FIGS. 30 and 32 show handles 456, 466. The handle 456 shown in FIG. 30 is inline with the body 450' of the cartridge 450. The handle 466 of FIG. 32 is perpendicular with the body 450' of the cartridge 450 and, therefore, functions as a stabilizing structure. FIG. 34 shows finger holder 476 gripping structures on the ends of the body 470' of the cartridge 470. The finger holders 476 would be suitable for gripping between a thumb and an index finger. FIG. 35 also shows finger holders. There may also be indented grips (shown as the concave base of the handle 456 shown in FIG. 30) which may also be indentations in the body of the cartridge (not shown). Although only some of the cartridges are shown with gripping structure, other cartridges could include gripping structure.

FIGS. 32 and 35 both show cartridges 460, 480 that include stabilizing structure (e.g. a stabilizer or foot) to help hold the cartridges 460, 480 upright while the clip is being removed. The handle 466 shown in FIG. 32 is perpendicular with the body 460' of the cartridge 460 and, therefore, functions as a stabilizing structure. The arced base structure 486 (also referred to as a "stabilizer") shown in FIG. 35 is associated with the body 480' of the cartridge 480. Because the arced base structure 486 increases the surface area of the base, it functions as a stabilizing structure. Although only a few cartridges are shown with stabilizers, other cartridges could include stabilizers.

Figure 29:
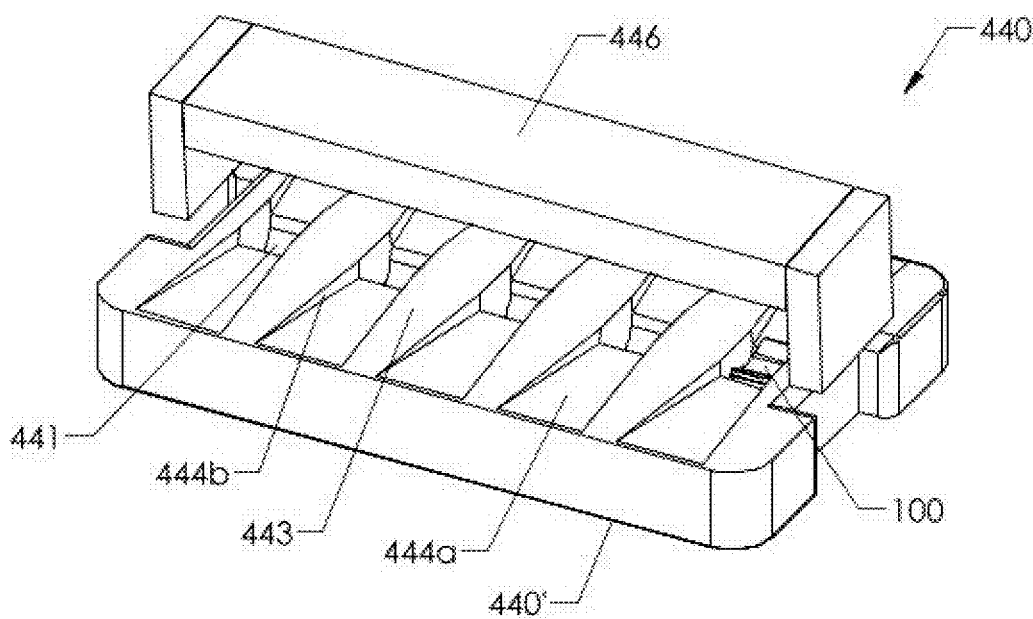
FIG. 29 is a perspective view of an exemplary cartridge with a clip securer over a plurality of formation wells.

Another optional feature is a clip securing structure (securer) that provides an additional mechanism to retain and secure the clips within the formation well(s) (e.g. for curing, packaging, storage, and/or shipping). FIG. 29 shows one type of securer 446. This securer 446 (the top piece of a two-piece construction) covers the formation wells 441 in the body 440' of the cartridge 440 (the bottom piece of a two-piece construction). The securer 446 may snap together with the cartridge 440. It should be noted that the securer/cartridge may be a single piece (e.g. folding) construction or may include multiple pieces (e.g. a separate securer for each formation well). It should be noted that the connection may be a snap fit or other known types of connections (e.g. pressure fit or with mechanical connectors). Although only one cartridge is shown with a securer, other cartridges could include a securer.

As mentioned, each of the shown cartridges 400, 405, 410, 418, 420, 440, 450, 460, 470, 480 include their own respective array of features. Although not exhaustive, the following paragraphs highlight some of the features of each shown cartridge.

FIGS. 23-24 shows an exemplary cartridge 400 with a single elongated channel formation well 401. Side channels 404b run parallel along both sides of the elongated channel formation well 401. The side channels 404b allow the applier (not shown) to grip clip wings 140 and 142 in order to remove the clip 100 from the cartridge 400. The upper surface of the cartridge 400 is angled (angled surfaces 404a) toward the single elongated channel formation well 401 to guide the pinching tips (not shown) toward the clip 100. Clips 100 can be side-loaded (loaded horizontally) into one side of the single elongated channel formation well 401. If there is an optional blocking structure such as the blocking structure 406 shown in FIG. 25, the clips 100 would be prevented from sliding out of the side opposite the loading side.

FIG. 25 shows a cartridge 405 similar to the cartridge 400 of FIG. 23, but with blocking structure 406 (shown blocking one end of an elongated channel formation well 407 and side channels 408). The cartridge 405 has a body 405' into which the elongated channel formation well 407 and side channels 408 are formed. The elongated channel formation well 407 and side channels 408 are shown as being at least approximately centered along the longitudinal center of the body 405' with flat upper surfaces 409 on either side thereof. The exemplary blocking structure 406 is at one end of the elongated channel formation well 407. As shown, the side channels 408 may also be blocked at one end.

Figure 26B:
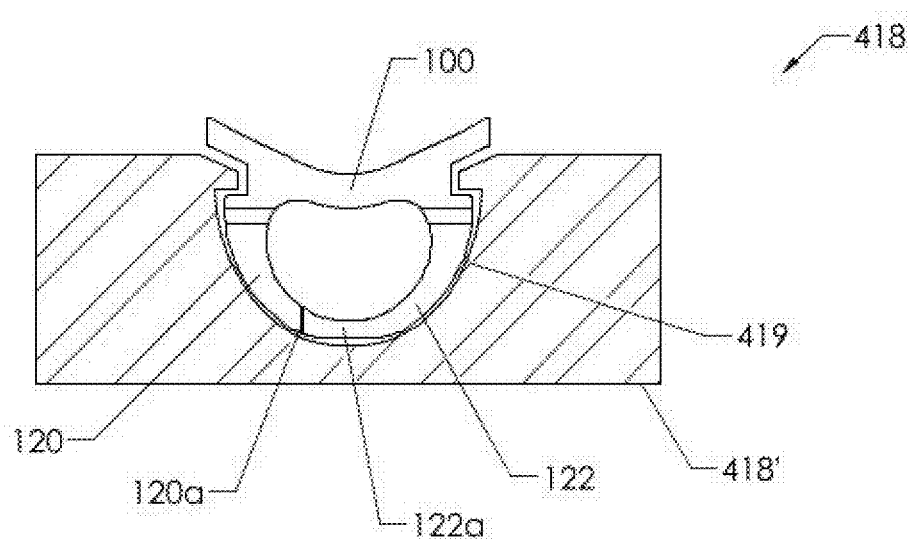
FIG. 26B is a cross-sectional view of a cartridge with a cartridge formation well with rounded well surfaces and an overhang.

FIG. 26A shows a cartridge 410 with a cartridge formation well 411 with angled well surfaces 412 and an overhang 416. As shown, the well surfaces 412 of the formation well 411 hold the sides 120 and 122 of the clips 100 in the closed position with the teeth 120a and 122a touching. The overhang was intended to hold the clip 100 in place in the closed position during annealing. The upper surface of the cartridge 410 is angled (angled surfaces 414a) toward the formation well 411 to guide the pinching tips toward the clip 100. FIG. 26B shows a cartridge 418 that is similar to cartridge 410 except that the well surfaces 419 are rounded.

Figure 27:
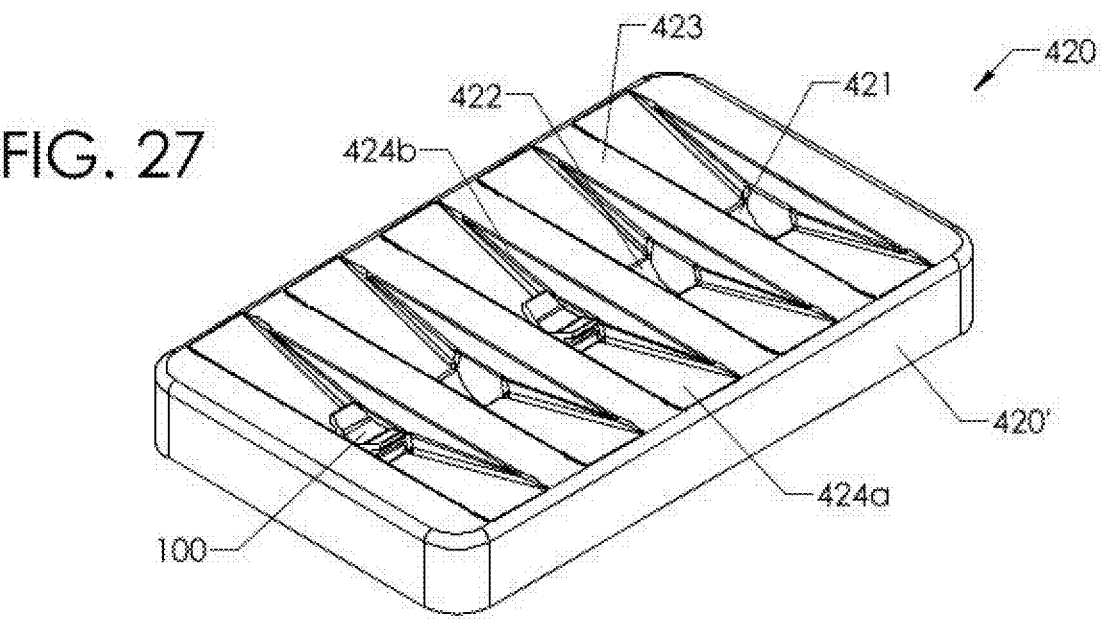
FIG. 27 is a perspective view of an exemplary cartridge with a plurality of formation wells.
Figure 28:
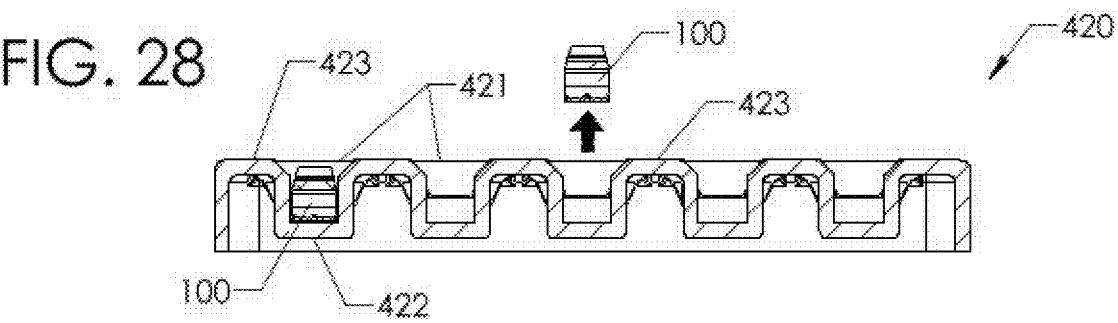
FIG. 28 is a cross-sectional view of a partial exemplary cartridge with a plurality of formation wells with a clip in a formation well and one clip being vertically removed.

FIGS. 27 and 28 show an exemplary cartridge 420 with a plurality of formation wells 421 (shown as five "pockets"). Between the formation wells 421 are dividers 423 that are designed to "grip" the opposing faces 130 and 132 (FIGS. 1A-1B and FIGS. 2A-2B) of the clip 100 to assist in holding the clips 100. The clips 100 may be "press fit" into the formation wells 421 because the formation wells 421 are the same width as or have a slightly smaller width than the width of the clip 100. This allows the clip 100 to be compressed slightly and held in place by the dividers 423 (or the ends of the cartridge 420). The spring nature of the clips also help to hold them in place. Put another way, when the clips are pressed into the fully closed position (closing the gap completely) there is a slight outward pressure that holds the clips inside their respective formation wells.

FIG. 29 shows an exemplary cartridge 440 with a clip securer 446 over a plurality of formation wells 441. This is shown as a two-piece construction with the securer 446 being the top piece and the cartridge 440 being the bottom piece. The securer 446 may snap together with the cartridge 440. The securer 446 can be removed in the operating room when the clips are needed for surgery.

Figure 31:
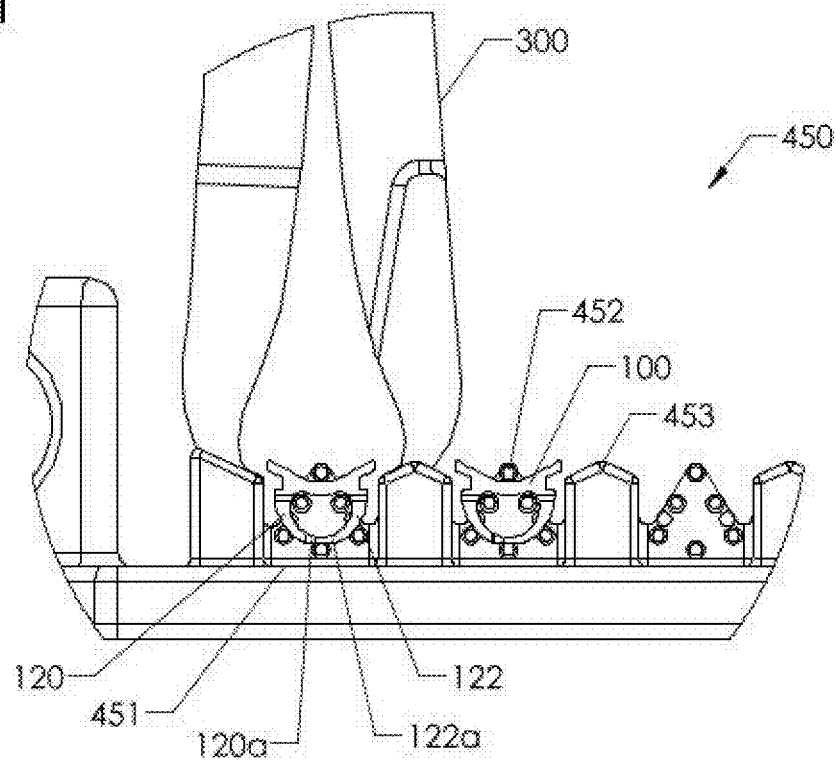
FIG. 31 is a side view of a detail of the exemplary cartridge of FIG. 30 with clips in formation wells, an applier beginning to remove one clip.

FIGS. 30 and 31 show an exemplary cartridge 450 with a plurality of formation wells 451. Each formation well 451 is shown as including formation structure 452 (formation pins 452). The formation pins 452 are shown as being both inside and outside of the clip 100. The formation pins 452 may bend or break to allow vertical clip removal. The cartridge 450 is shown as having a handle 456 inline with the cartridge body 450'. Clips can be side-loaded into one side of their respective formation wells 451 but, because of the shown blocking structures 455, are prevented from sliding out of the opposite side.

Figure 33:
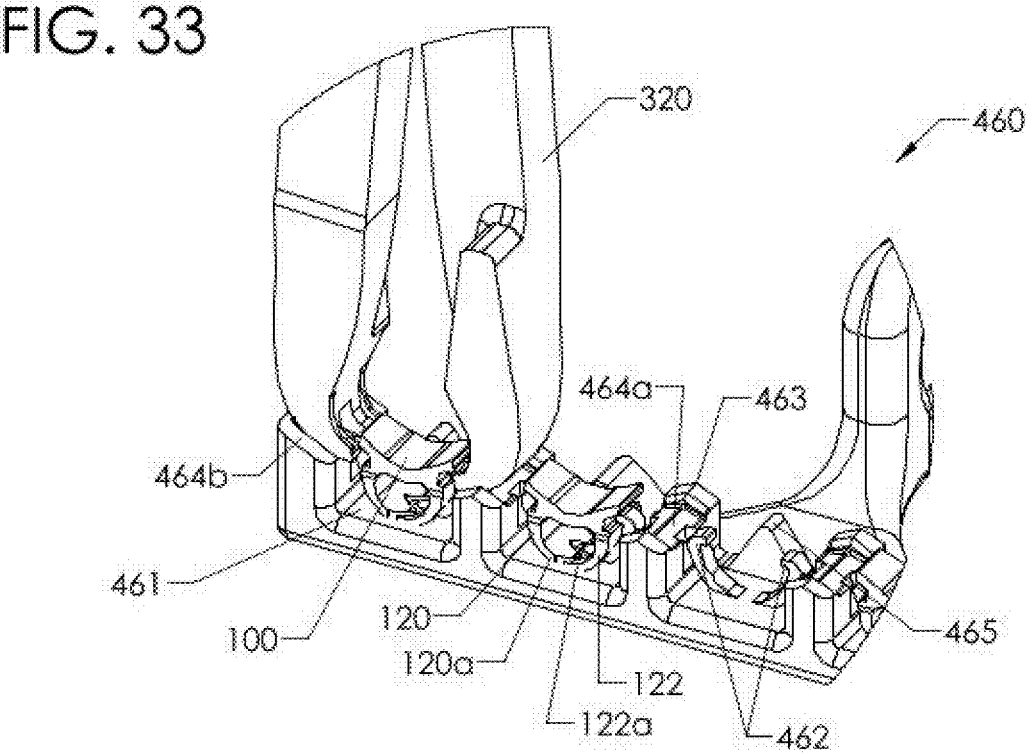
FIG. 33 is a perspective view of a detail of the exemplary cartridge of FIG. 32 with clips in formation wells, an applier beginning to remove one clip.

FIGS. 32 and 33 show an exemplary cartridge 460 with a plurality of formation wells 461. Each formation well 461 is shown as including formation structure 462 (formation fingers 462). The formation fingers 462 are shown as being on both sides of the clip 100 such that they hold the clips and/or hold the clips 100 in the closed position for curing and also help hold the clip for packaging, storage, and/or shipping. The formation fingers 462 either bend or break to allow vertical clip removal. The cartridge 460 is shown as having a handle 466 perpendicular with the cartridge body 460'. The perpendicular handle 466 also functions as a stabilizer. Clips can be side-loaded into one side of their respective formation wells 461 but, because of the shown blocking structures 465, are prevented from sliding out of the opposite side.

FIG. 34 shows an exemplary cartridge 470 with finger holders 476 at both ends.

FIG. 35 shows an exemplary cartridge 480 with handles at both ends and arced base structure 486 on both sides of the body 480' of the cartridge 480.

The cartridges may be single use or reusable. They are preferably made from medical grade cartridge materials including metals (e.g. stainless steel, titanium, aluminum), plastics (e.g. acrylic, polycarbonate, polypropylene, nylon, PEEK, polysulfone), and/or other cartridge materials suitable for use in medical applications. Preferred cartridge material would be polypropylene or other somewhat soft/flexible material. Other preferred cartridge material would be somewhat rigid material into which the clips may be "snapped-in" and out of which the clips may be "snapped-out." If the cartridges are reusable cartridges, the cartridge material is preferably re-sterilizable. The finish on the form wells is preferably a rough or matte textured finish because it provides extra friction to help hold clips within the form wells.

Packaging may allow many cartridges to be processed together and then separated (maybe through perforations) for final individual packaging.

Systems and Methods

FIGS. 36-50 provide an illustrative timeline of exemplary interactions between exemplary clips, appliers, and/or cartridges as they might be used. The shown clips, appliers, and/or cartridges may be substituted with other shown and/or described clips, appliers, and/or cartridges.

Although not specifically represented in the figures, if any of the components are individually packaged (e.g. a pre-packaged cartridge that has clips loaded therein), they may be removed from their package in the operating room (OR) by the surgeon or surgical tech. If there is a securer associated with a cartridge, that securer could be removed in the operating room when the clips are needed for surgery.

Figure 36:
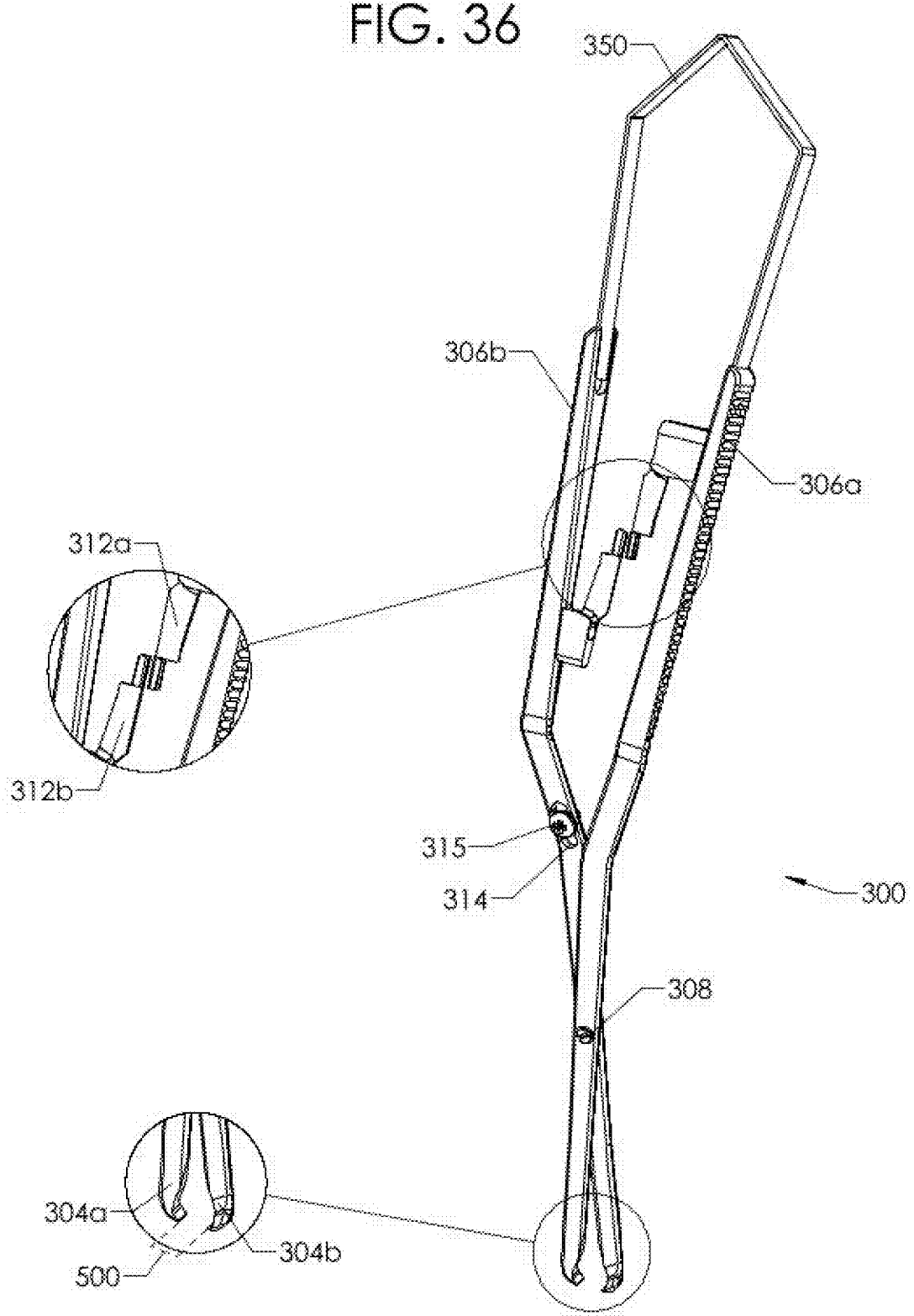
FIG. 36 is a perspective view of an applier in the un-pinched stage.

FIG. 36 shows an exemplary applier 300 in the un-pinched stage (which can be thought of as the neutral or released stage). In this un-pinched stage both the applier pinching tips 304a-b and the handles 306a-b are relatively far apart (the distance 500 between the tips has been widened or increased). The distance 500 between the applier pinching tips 304a-b is sufficiently wide to pass over the clip wings 140 and 142 (FIGS. 1A-1B and FIGS. 2A-2B). The lock 312a-b is unengaged (unlocked).

FIGS. 37-42 show the applier 300 in (or moving toward) the partially-pinched stage (which can be thought of as the removal or carrying stage). Applying a "medium" amount of inward pressure (shown as single arrows in FIG. 40) to the handles 306a-b causes the applier 300 to transition from the un-pinched stage into the partially-pinched stage. In this transition, the applier pinching tips 304a-b and the handles 306a-b move (or have moved) closer together (as compared to the un-pinched stage) such that they are only partially spread (FIG. 41). As shown in FIGS. 37-38, guided by the guide and/or access structure (shown as the angled surfaces 424a and the wall guides 424b) of the exemplary cartridge 420, the distance 510 between the applier pinching tips 304a-b narrows so that the applier pinching tips 304a-b engage the clip grooves 150 and 152 (FIGS. 1A-1B and FIGS. 2A-2B). To be clear, the distance 510 is smaller than the distance 500 (FIG. 36). Further, in the partially-pinched stage, the lock 312a-b is engaged (FIG. 42). With the pinching tips 304a-b engaging the clip grooves 150 and 152 (as shown in FIGS. 37 and 38), the partially-pinched applier 300 can be used to lift a single clip 100 from a cartridge 420 (FIGS. 39 and 41). Because the lock 312a-b is engaged (FIG. 42), the clip 100 is held and can be carried by the applier 300 without the user needing to continue to exert force on the handles 306a-b. Put another way, although the applier 300 could be held by a surgical tech, it could also be placed on the table until the surgeon needs it.

FIGS. 43-47 show the applier 300 in (or moving toward) the pinched stage (which can be thought of as the clip opening stage). Applying a "maximum" amount of inward pressure (shown as double arrows in FIG. 43) to the handles 306a-b causes the applier 300 to transition from the partially-pinched stage to the pinched stage. In this transition, the applier pinching tips 304a-b and the handles 306a-b move (or have moved) closer together (as compared to the partially-pinched stage) such that they apply pressure to the clip grooves 150 and 152 (FIGS. 1A-1B and FIGS. 2A-2B). The lock 312a-b may be unengaged (unlocked) as the applier 300 transitions to the pinched stage. The distance 520 between the pinching tips 304a-b shown in FIG. 44 is smaller than the distance 510 between the pinching tips 304a-b shown in FIG. 41. The distance between the applier pinching tips 304a-b may be limited by the optional limiter 314 to prevent the pinching tips 304a-b from damaging the clip 100 (over-opening or otherwise experiencing plastic deformation) by squeezing it too hard. As set forth above, in the pinched stage, the pinching tips 304a-b apply pressure to the grooves 150 and 152 (FIGS. 1A-1B and FIGS. 2A-2B) of the clip 100 which, in turn, causes the sides 120 and 122 of the clip 100 to spread to the open position (FIG. 44) in which the distance between the teeth 120a and 122a is increased (the spread gap 124b as shown in FIGS. 2A and 2B). In a clip that is roughly 3.0 mm×4.0 mm×5.0 mm, the spread gap 124b may be, for example, approximately 2.0 mm to 3.0 mm (ideally approximately 2.5 mm). In the open position, the clip 100 is ready to be applied to the everted ends of the tissue 600.

Figure 47:
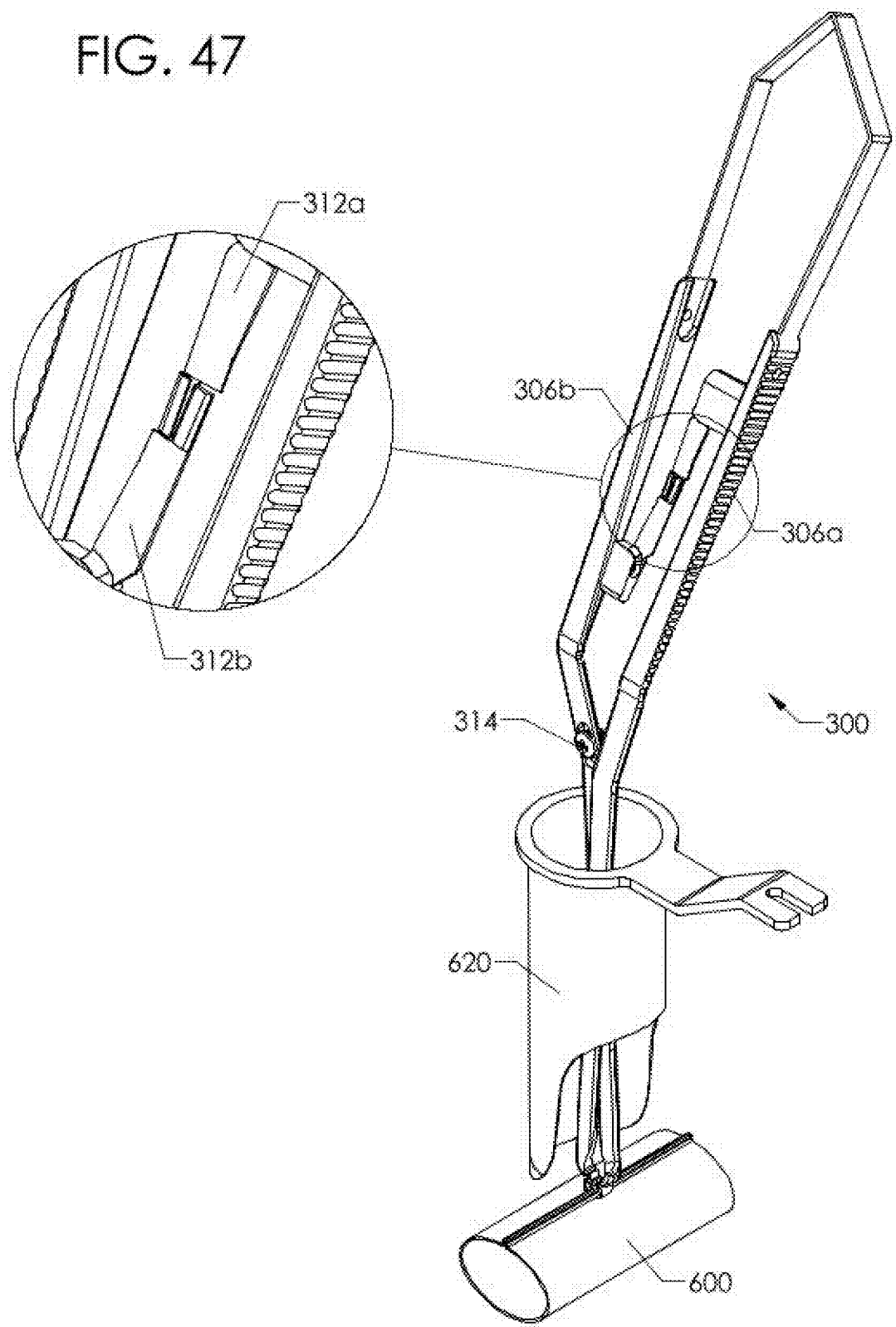
FIG. 47 is a perspective view of the applier in the pinched stage applying a clip to close tissue through a cannula.

During open surgery, forceps (not shown) may be used to approximate the everted tissue ends 600. As the surgeon continues to squeeze the handles 306a-b, the clip 100 is held in the open position. Then, using the applier 300 in the pinched stage, the open clip 100 is applied to the everted ends of the tissue 600 to "close" the tissue. FIGS. 45-46 show the application of the clip 100. FIG. 47 shows the applier 300 in the pinched stage applying a clip 100 to close the tissue 600 through an exemplary cannula 620 (a narrow tube—the bottom of the tube being removed in the drawing to show the applier and the clip) used in minimally invasive surgery (MIS). The surgeon lowers the applier 300 in the partially-pinched stage into the tube and then squeezes the handles 306a-b together (transitioning the applier 300 to the pinched stage) to apply the clip 100 to the everted ends of the tissue 600.

Figure 48:
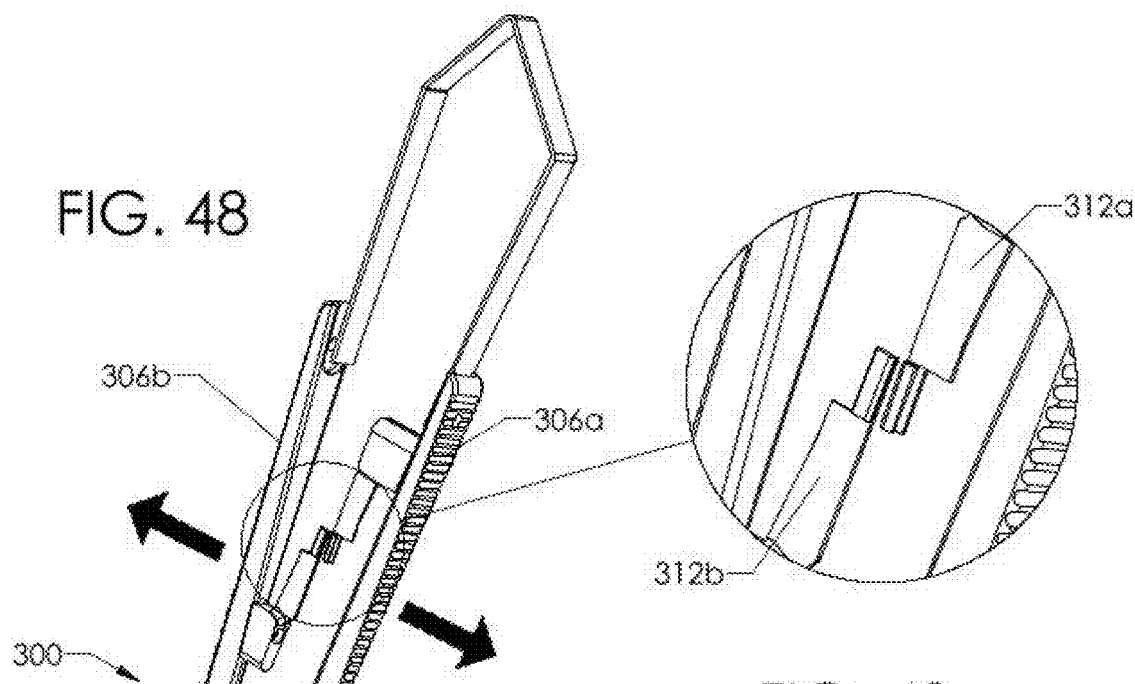
FIG. 48 is a perspective view of the applier after pressure is no longer being applied to the handles so that the applier returns to the un-pinched stage and the pinching tips release the clip.
Figure 49:
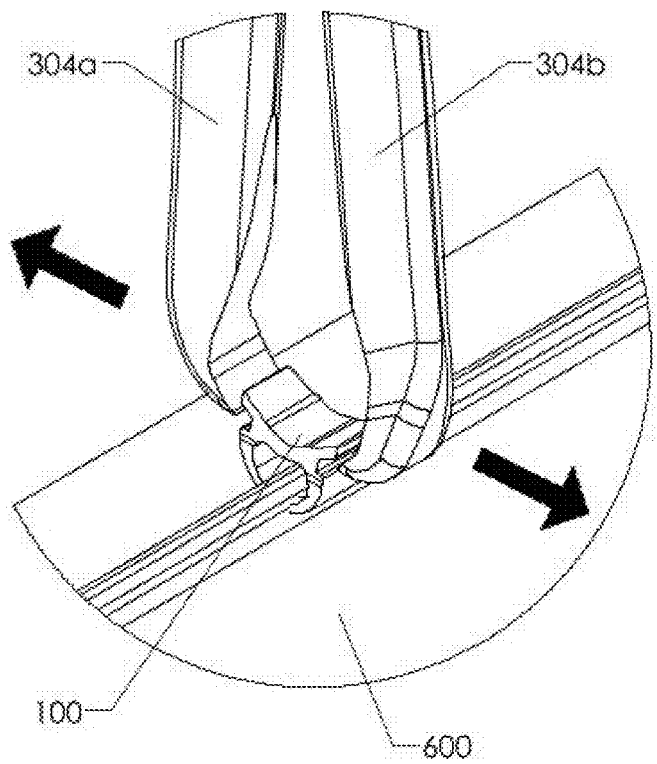
FIG. 49 is a perspective detailed view of the pinching tips returning to the un-pinched stage and releasing the clip, the clip remaining closed so as to hold the tissue together.
Figure 50:
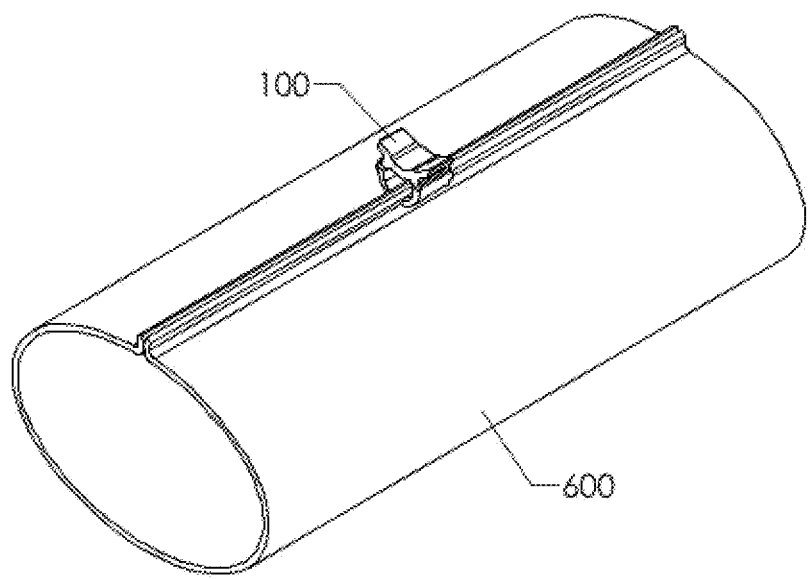
FIG. 50 is a perspective view of the clip in the closed position holding the tissue together.

After the clip 100 has been positioned, the surgeon releases the handles 306a-b (releasing the "squeezing force" shown by the outward arrows) to release the clip 100 which remains on the everted ends of the tissue 600 and secures them together. FIGS. 48 and 49 show the applier 300 after pressure is no longer being applied to the handles 306a-b so that the applier 300 returns to the un-pinched stage and the pinching tips 304a-b release the clip 100. Once released, the clip 100 closes automatically using the inherent spring force of the design/material combination. As the distance 500 between the pinching tips 304a-b is sufficiently wide to pass over the clip wings 140 and 142 (FIGS. 1A-1B and FIGS. 2A-2B), the applier 300 can be removed from the clip 100, leaving the clip 100 to secure the everted ends of the tissue 600 (creating a tissue closure) as shown in FIG. 50. Additional clips 100 may be applied as needed.

The description of the clips, appliers, cartridges, and methods and systems associated therewith, uses terminology that should be clarified. Please note that the terms and phrases may have additional definitions and/or examples throughout the specification. Where otherwise not specifically defined, words, phrases, and acronyms are given their ordinary meaning in the art. The following paragraphs provide basic parameters for interpreting terms and phrases used herein.

The term "associated" is defined to mean integral or original, retrofitted, attached, connected (including functionally connected), located near, and/or accessible by. For example, if a lock part is "associated" with a shaft, it may be (for example) integral with the shaft, directly attached to the shaft, or indirectly attached to the shaft.

It should be noted that relative terms are meant to help in the understanding of the technology and are not meant to limit the scope of the invention. Similarly, unless specifically stated otherwise, the terms "first," "second," and "third" are meant solely for purposes of designation and not for order or limitation. For example, the "first shaft" has no order relationship with the "second shaft."

It should be noted that some terms used in this specification are meant to be relative. For example, the term "top" is meant to be relative to the term "bottom." Similarly, the term "front" is meant to be relative to the term "back," and the term "side" is meant to describe a "face" or "view" that connects the "front" and the "back." Rotation of the system or component that would change the designation might change the terminology but not the concept.

Terms such as "may," "might," "can," and "could" are used to indicate alternatives and optional features and only should be construed as a limitation if specifically included in the claims. It should be noted that the various components, features, steps, or embodiments thereof are all "preferred" whether or not it is specifically indicated. Claims not including a specific limitation should not be construed to include that limitation.

Unless specifically stated otherwise, the term "exemplary" is meant to indicate an example, representation, and/or illustration of a type. The term "exemplary" does not necessarily mean the best or most desired of the type.

It should be noted that, unless otherwise specified, the term "or" is used in its nonexclusive form (e.g. "A or B" includes, but is not limited to, A, B, A and B, or any combination thereof). It should be noted that, unless otherwise specified, "and/or" is used similarly (e.g. "A and/or B" includes, but is not limited to, A, B, A and B, or any combination thereof). It should be noted that, unless otherwise specified, the terms "includes," "has," and "contains" (and variations of these terms) mean "comprises" (e.g. a device that "includes," "has," or "contains" A and B, comprises A and B, but optionally may contain C or additional components other than A and B).

It should be noted that, unless otherwise specified, the singular forms "a," "an," and "the" refer to one or more than one, unless the context clearly dictates otherwise. Similarly, unless specifically limited, the use of singular language (e.g. "component," "module," or "step") may include plurals (e.g. "components," "modules," or "steps"), unless the context clearly dictates otherwise.

It is to be understood that the inventions, examples, and embodiments described herein are not limited to particularly exemplified materials, methods, and/or structures. It is to be understood that the inventions, examples, and embodiments described herein are to be considered preferred inventions, examples, and embodiments whether specifically identified as such or not. The shown inventions, examples, and embodiments are preferred, but are not meant to be limiting unless specifically claimed, in which case they may limit the scope of that particular claim.

It is to be understood that for methods or procedures disclosed herein that include one or more steps, actions, and/or functions for achieving the described actions and results, the methods' steps, actions, and/or functions may be interchanged with one another without departing from the scope of the present invention. In other words, unless a specific order of steps, actions, and/or functions is required for proper or operative operation of the methods or procedures, the order and/or use of specific steps, actions, and/or functions may be modified without departing from the scope of the present invention.

All references (including, but not limited to, publications, patents, and patent applications) cited herein, whether supra or infra, are hereby incorporated by reference in their entirety.

The terms and expressions that have been employed in the foregoing specification are used as terms of description and not of limitation, and are not intended to exclude equivalents of the features shown and described. While the above is a complete description of selected embodiments of the present invention, it is possible to practice the invention using various alternatives, modifications, adaptations, variations, and/or combinations and their equivalents. It will be appreciated by those of ordinary skill in the art that any arrangement that is calculated to achieve the same purpose may be substituted for the specific embodiment shown. It is also to be understood that the following claims are intended to cover all of the generic and specific features of the invention herein described and all statements of the scope of the invention that, as a matter of language, might be said to fall therebetween.

What is claimed is:

1. An applier for manipulating clips, said appliers comprising:
   (a) a first shaft having a first pinching tip at least substantially at a first shaft tip end, a first handle at least substantially at a first shaft handle end, and a first shaft midpoint between said first shaft tip end and said first shaft handle end;
   (b) a second shaft having a second pinching tip at least substantially at a second shaft tip end, a second handle at least substantially at a second shaft handle end, and a second shaft midpoint between said second shaft tip end and second shaft said handle end;
   (c) a securing pivot pivotally connecting said first shaft and said second shaft at said first shaft midpoint and said second shaft midpoint;

(d) an engageable and disengageable lock, said lock substantially preventing said handles from spreading when said lock is engaged; and
(e) said applier having at least three stages, comprising:
  (i) an un-pinched stage in which said first pinching tip is relatively far from said second pinching tip, said first handle is relatively far from said second handle, and said lock is unengaged;
  (ii) a pinched stage in which said first pinching tip is relatively close to said second pinching tip, said first handle is relatively close to said second handle, and said lock is unengaged; and
  (iii) a partially-pinched stage in which said first pinching tip is at an in-between distance from said second pinching tip, said first handle is at an in-between distance from said second handle, and said lock is engaged.

2. The applier of claim 1, each said pinching tip being an inwardly-angled pinching tip.

3. The applier of claim 1 further comprising an expander for encouraging increasing distance between the handle of a first shaft and the handle of a second shaft, said engageable and disengageable lock positioned between said securing pivot and said expander.

4. The applier of claim 1 wherein said engageable and disengageable lock is a two-part lock, a first lock part associated with said first shaft and a second lock part associated with said second shaft, said first lock part and said second lock part engaging and disengaging using an off-planar movement.

5. The applier of claim 1 further comprising an expander for encouraging increasing distance between the handle of said first shaft and the handle of said second shaft, said expander attached to an end of said first handle of said first shaft and to an end of said second handle of said second shaft.

6. The applier of claim 1 wherein, when engaged, said lock maintains the applier in the partially-pinched stage, thereby preventing the expander from increasing distance between the handle of said first shaft and the handle of said second shaft.

7. The applier of claim 1 further comprising a limiter for limiting the distance between said first pinching tip and said second pinching tip.

8. The applier of claim 1 further comprising an adjustable limiter for limiting the distance between said first pinching tip and said second pinching tip.

9. The applier of claim 1 further comprising:
(a) a limiter for limiting the distance between said first pinching tip and said second pinching tip, said limiter positioned along at least one of said first and second shafts; and
(b) an expander for encouraging increasing distance between the handle of said first shaft and the handle of said second shaft; and
(c) said limiter positioned between said securing pivot and said expander.

10. The applier of claim 1 further comprising:
(a) an adjustable limiter for limiting the distance between said first pinching tip and said second pinching tip; and
(b) said adjustable limiter including a slot and a location fixer associated with one of said shafts.

11. The applier of claim 1, said first shaft being angled and said second shaft being angled.

12. The applier of claim 1 further comprising:
(a) said first shaft having at an approximately 30 degree angle; and
(b) said second shaft having at an approximately 30 degree angle.

13. The applier of claim 1, further comprising:
(a) a limiter for limiting the distance between said first pinching tip and said second pinching tip;
(b) said first shaft having a bend between said engageable and disengageable lock and said limiter; and
(c) said second shaft having a bend between said engageable and disengageable lock and said limiter.

14. An applier for manipulating clips, said appliers comprising:
(a) a first shaft having a first pinching tip at least substantially at a first shaft tip end, a first handle at least substantially at a first shaft handle end, and a first shaft midpoint between said first shaft tip end and said first shaft handle end;
(b) a second shaft having a second pinching tip at least substantially at a second shaft tip end, a second handle at least substantially at a second shaft handle end, and a second shaft midpoint between said second shaft tip end and second shaft said handle end;
(c) a securing pivot pivotally connecting said first shaft and said second shaft at said first shaft midpoint and said second shaft midpoint; and
(d) a limiter for limiting the distance between said first pinching tip and said second pinching tip.

15. The applier of claim 14, further comprising:
(a) said first shaft having a first bent central shaft portion;
(b) said second shaft having a second bent central shaft portion; and
(c) when said first shaft and said second shaft overlap, said first bent central shaft portion and said second bent central shaft portion define a central opening therebetween.

16. The applier of claim 14, further comprising an expander for encouraging increasing distance between the handle of said first shaft and the handle of said second shaft, said limiter positioned along at least one of said first and second shafts, and said limiter positioned between said securing pivot and said expander.

17. The applier of claim 14, wherein said limiter is an adjustable limiter.

18. The applier of claim 14 further comprising:
(a) said limiter being an adjustable limiter for limiting the distance between said first pinching tip and said second pinching tip; and
(b) said adjustable limiter including a slot and a location fixer associated with one of said shafts.

19. The applier of claim 14 further comprising:
(a) an expander for encouraging increasing distance between the handle of a first shaft and the handle of a second shaft;
(b) an engageable and disengageable lock, said lock substantially preventing said handles from spreading when said lock is engaged; and
(c) said engageable and disengageable lock positioned between said securing pivot and said expander.

20. The applier of claim 14 further comprising:
(a) an engageable and disengageable lock having a first lock part associated with said first shaft and a second lock part associated with said second shaft; and
(b) said first lock part and said second lock part engaging and disengaging using an off-planar movement.

21. The applier of claim 14, said first shaft being angled and said second shaft being angled.

22. The applier of claim 14 further comprising:
(c) said first shaft having at an approximately 30 degree angle; and
(d) said second shaft having at an approximately 30 degree angle.

23. The applier of claim 14, further comprising:
(a) said first shaft having a bend between said engageable and disengageable lock and said limiter; and
(b) said second shaft having a bend between said engageable and disengageable lock and said limiter.

24. An applier for manipulating medical devices, said appliers comprising:
(a) a first shaft having a first pinching tip at least substantially at a first shaft tip end, a first handle at least substantially at a first shaft handle end, and a first shaft midpoint between said first shaft tip end and said first shaft handle end;
(b) a second shaft having a second pinching tip at least substantially at a second shaft tip end, a second handle at least substantially at a second shaft handle end, and a second shaft midpoint between said second shaft tip end and second shaft said handle end;
(c) a securing pivot pivotally connecting said first shaft and said second shaft at said first shaft midpoint and said second shaft midpoint;
(d) an engageable and disengageable lock, said lock substantially preventing said handles from spreading when said lock is engaged;
(e) said applier having at least three stages, comprising:
  (i) an un-pinched stage in which said first pinching tip is relatively far from said second pinching tip, said first handle is relatively far from said second handle, and said lock is unengaged;
  (ii) a pinched stage in which said first pinching tip is relatively close to said second pinching tip, said first handle is relatively close to said second handle, and said lock is unengaged; and
  (iii) a partially-pinched stage in which said first pinching tip is at an in-between distance from said second pinching tip, said first handle is at an in-between distance from said second handle, and said lock is engaged;
(f) at least one of said medical devices formed using a medical device forming method, the method comprising the steps of:
  (i) receiving a no more than partially cured rubbery device with a gap defined therein;
  (ii) placing said no more than partially cured rubbery device in a form such that said gap is closed; and
  (iii) curing said no more than partially cured rubbery device such that it becomes a flexible but rigid device; and
(g) a cartridge for holding at least one of said medical devices, said cartridge comprising:
  (i) a cartridge body;
  (ii) at least one formation well defined within said body; and
  (iii) each said at least one formation well sized and shaped to hold at least one of said medical devices in a closed position with teeth of opposing sides touching; and
(h) wherein said applier may be used to remove at least one said medical device from said cartridge.

25. An applier for manipulating medical devices, said appliers comprising:
(a) a first shaft having a first pinching tip at least substantially at a first shaft tip end, a first handle at least substantially at a first shaft handle end, and a first shaft midpoint between said first shaft tip end and said first shaft handle end;
(b) a second shaft having a second pinching tip at least substantially at a second shaft tip end, a second handle at least substantially at a second shaft handle end, and a second shaft midpoint between said second shaft tip end and second shaft said handle end;
(c) a securing pivot pivotally connecting said first shaft and said second shaft at said first shaft midpoint and said second shaft midpoint;
(d) a limiter for limiting the distance between said first pinching tip and said second pinching tip;
(e) at least one of said medical devices formed using a medical device forming method, the method comprising the steps of:
  (i) receiving a no more than partially cured rubbery device with a gap defined therein;
  (ii) placing said no more than partially cured rubbery device in a form such that said gap is closed; and
  (iii) curing said no more than partially cured rubbery device such that it becomes a flexible but rigid device; and
(f) a cartridge for holding at least one of said medical devices, said cartridge comprising:
  (i) a cartridge body;
  (ii) at least one formation well defined within said body; and
  (iii) each said at least one formation well sized and shaped to hold at least one of said clips in medical devices in a closed position with teeth of opposing sides touching; and
(g) wherein said applier may be used to remove at least one said medical device from said cartridge.

26. The applier of claim 25, wherein said limiter is an adjustable limiter.

* * * * *